(12) United States Patent
Benton et al.

(10) Patent No.:  US 12,630,793 B2
(45) **Date of Patent:  \*May 19, 2026**

(54) METHODS OF USING PIPE-BASED BIOREACTORS FOR PRODUCING COMESTIBLE MEAT PRODUCTS

(71) Applicant: Upside Foods, Inc., Berkeley, CA (US)

(72) Inventors: Charles Knight Benton, Berkeley, CA (US); Konrad Müller-Auffermann, Emeryville, CA (US)

(73) Assignee: Upside Foods, Inc., Emeryville, CA (US)

( \* ) Notice: Subject to any disclaimer, the term of this patent is extended or adjusted under 35 U.S.C. 154(b) by 0 days.

This patent is subject to a terminal disclaimer.

(21) Appl. No.: 18/627,047

(22) Filed: Apr. 4, 2024

(65) Prior Publication Data

US 2024/0271067 A1     Aug. 15, 2024

Related U.S. Application Data

(63) Continuation of application No. 18/047,545, filed on Oct. 18, 2022, now Pat. No. 11,987,778, which is a
(Continued)

(51) Int. Cl.
*C12M 1/00*          (2006.01)
*A22C 17/00*        (2006.01)
(Continued)

(52) U.S. Cl.
CPC ......... *C12M 23/06* (2013.01); *A22C 17/0006* (2013.01); *C12M 23/58* (2013.01);
(Continued)

(58) Field of Classification Search
CPC ............................. C12M 23/06; C12M 25/14
See application file for complete search history.

(56) References Cited

U.S. PATENT DOCUMENTS 3,193,460 A     7/1965  Krabbe et al.
3,905,865 A     9/1975  Mcaleer et al.
(Continued)

FOREIGN PATENT DOCUMENTS

CN          1350433 A       5/2002
CN         101132803 A      2/2008
(Continued)

OTHER PUBLICATIONS

Examination Report as received in Australian application 2023200307 dated Oct. 8, 2024.
(Continued)

*Primary Examiner* — Nathan A Bowers
(74) *Attorney, Agent, or Firm* — Keller Preece PLLC

(57)          ABSTRACT

The present disclosure relates to systems, apparatuses, and methods for preparing cell-based meat products (i.e., comestible meat products). In particular, a pipe-based bioreactor is disclosed having one or more substrates disposed therein. In one or more embodiments, the one or more substrates comprise a plurality of nominally spaced substrates conforming to an interior profile of an elongated enclosure of the pipe-based bioreactor. In some embodiments, multiple pipe-based bioreactors are interconnected a fluid source for preparing cell-based meat products. In addition, various methods and procedures for utilizing embodiments of pipe-based bioreactors are disclosed.

20 Claims, 25 Drawing Sheets

Related U.S. Application Data continuation of application No. 18/047,196, filed on Oct. 17, 2022, now Pat. No. 11,981,884.

(51) Int. Cl.

| | |
|---|---|
| *C12M 1/12* | (2006.01) |
| *C12M 3/00* | (2006.01) |
| *C12M 3/04* | (2006.01) |
| *A23L 13/00* | (2016.01) |

(52) U.S. Cl.
CPC ............ *C12M 25/14* (2013.01); *C12M 27/10* (2013.01); *A23L 13/00* (2016.08); *A23V 2002/00* (2013.01)

(56) References Cited

U.S. PATENT DOCUMENTS

| | | | |
|---|---|---|---|
| 4,080,258 | A | 3/1978 | McAleer et al. |
| 4,343,904 | A | 8/1982 | Birch et al. |
| 4,379,846 | A | 4/1983 | Shkidchenko et al. |
| 4,508,819 | A | 4/1985 | Rose |
| 4,904,600 | A | 2/1990 | Ramp |
| 5,266,476 | A | 11/1993 | Sussman et al. |
| 5,320,963 | A | 6/1994 | Knaack et al. |
| 5,585,266 | A | 12/1996 | Plitt et al. |
| 5,650,325 | A | 7/1997 | Spielmann |
| 5,656,421 | A | 8/1997 | Gebhard et al. |
| 5,705,390 | A | 1/1998 | Kadouri et al. |
| 5,786,215 | A | 7/1998 | Brown et al. |
| 6,197,575 | B1 | 3/2001 | Griffith et al. |
| 6,835,390 | B1 | 12/2004 | Vein |
| 7,875,448 | B2 | 1/2011 | Furey |
| 8,294,632 | B2 | 10/2012 | Skarp |
| 9,023,642 | B2 | 5/2015 | Kleis et al. |
| 9,249,383 | B2 | 2/2016 | Yu et al. |
| 9,657,266 | B2 | 5/2017 | Kasuto et al. |
| 9,969,966 | B2 | 5/2018 | Asgari |
| 9,994,812 | B2 | 6/2018 | Kim et al. |
| 11,147,300 | B2 | 10/2021 | Leung et al. |
| 11,193,102 | B2 | 12/2021 | Ohkubo |
| 2005/0084958 | A1 | 4/2005 | Vein |
| 2005/0095711 | A1 | 5/2005 | More |
| 2005/0287660 | A1 | 12/2005 | Aubry et al. |
| 2006/0019388 | A1 | 1/2006 | Hutmacher et al. |
| 2006/0172417 | A1 | 8/2006 | Rathenow et al. |
| 2007/0122901 | A1 | 5/2007 | Morita et al. |
| 2008/0009063 | A1 | 1/2008 | Okano et al. |
| 2008/0011766 | A1 | 1/2008 | Jordan et al. |
| 2008/0206735 | A1 | 8/2008 | Asgari |
| 2008/0208351 | A1 | 8/2008 | Besenbacher et al. |
| 2008/0293139 | A1 | 11/2008 | Watanabe |
| 2009/0120503 | A1 | 5/2009 | Donahue |
| 2009/0311777 | A1 | 12/2009 | Edwards et al. |
| 2010/0161954 | A1 | 6/2010 | Oyama |
| 2010/0184182 | A1 | 7/2010 | Hase |
| 2010/0196432 | A1 | 8/2010 | Feinberg et al. |
| 2010/0216242 | A1 | 8/2010 | Shimizu et al. |
| 2010/0330644 | A1 | 12/2010 | Feinberg et al. |
| 2011/0195462 | A1 | 8/2011 | Banks |
| 2011/0212493 | A1 | 9/2011 | Hirschel et al. |
| 2011/0263021 | A1 | 10/2011 | Stobbe |
| 2012/0129257 | A1 | 5/2012 | Yu et al. |
| 2013/0029008 | A1 | 1/2013 | Forgacs et al. |
| 2013/0059339 | A1 | 3/2013 | Karerangabo et al. |
| 2013/0168296 | A1 | 7/2013 | Swanda et al. |
| 2013/0196375 | A1 | 8/2013 | Strobbe |
| 2013/0323841 | A1 | 12/2013 | Kruglick |
| 2014/0093618 | A1 | 4/2014 | Forgacs et al. |
| 2014/0349385 | A1 | 11/2014 | Erdenberger et al. |
| 2015/0079238 | A1 | 3/2015 | Marga et al. |
| 2015/0125952 | A1 | 5/2015 | Kim et al. |
| 2015/0322397 | A1* | 11/2015 | Cornforth ............. C12M 25/14 435/293.1 |
| 2016/0222336 | A1 | 8/2016 | Lee et al. |
| 2016/0227830 | A1 | 8/2016 | Genovese et al. |

| | | | |
|---|---|---|---|
| 2016/0251625 | A1 | 9/2016 | Genovese et al. |
| 2017/0253849 | A1 | 9/2017 | Miller |
| 2017/0349873 | A1 | 12/2017 | Frank et al. |
| 2018/0187139 | A1 | 7/2018 | Patel |
| 2018/0214600 | A1 | 8/2018 | Magin et al. |
| 2018/0282678 | A1 | 10/2018 | Catillo et al. |
| 2019/0024079 | A1 | 1/2019 | Genovese et al. |
| 2019/0122239 | A1 | 4/2019 | Yoon |
| 2019/0213519 | A1 | 7/2019 | Metz et al. |
| 2019/0338232 | A1 | 11/2019 | Breemhaar et al. |
| 2020/0165569 | A1 | 5/2020 | Genovese et al. |
| 2021/0024868 | A1 | 1/2021 | Ferrie et al. |
| 2021/0106032 | A1 | 4/2021 | Leung et al. |
| 2021/0130760 | A1 | 5/2021 | Castillo et al. |
| 2021/0145031 | A1 | 5/2021 | Leung et al. |
| 2021/0171912 | A1 | 6/2021 | Genovese et al. |
| 2021/0401007 | A1 | 12/2021 | Leung et al. |
| 2021/0403848 | A1 | 12/2021 | Tsuzuki et al. |
| 2022/0056394 | A1 | 2/2022 | Leung et al. |
| 2022/0195359 | A1 | 6/2022 | Lavon et al. |
| 2022/0213427 | A1 | 7/2022 | Melchiorri |
| 2022/0361538 | A1 | 11/2022 | Leung et al. |
| 2022/0396756 | A1 | 12/2022 | Mouthuy |
| 2022/0401974 | A1 | 12/2022 | Liu et al. |
| 2023/0407224 | A1 | 12/2023 | Lavon et al. |

FOREIGN PATENT DOCUMENTS

| | | | |
|---|---|---|---|
| CN | 101646762 A | 2/2010 | |
| CN | 102232109 A | 11/2011 | |
| CN | 103747693 A | 4/2014 | |
| CN | 108025112 A | 5/2018 | |
| CN | 108697119 A | 10/2018 | |
| CN | 109154006 A | 1/2019 | |
| DE | 102008015633 A1 | 10/2009 | |
| EP | 2 736 357 B1 | 6/2014 | |
| JP | S62-087092 A | 4/1987 | |
| JP | 2005/080540 A | 3/2005 | |
| JP | 2008/011766 A | 1/2008 | |
| JP | 2010/161954 A | 7/2010 | |
| JP | 2017-176140 A | 10/2017 | |
| JP | 62-044173 A | 12/2017 | |
| JP | 2019/213519 A | 12/2019 | |
| JP | 2022-554013 A | 12/2022 | |
| KR | 10-2014-0040212 A | 4/2014 | |
| KR | 10-2018-0026792 A | 3/2018 | |
| KR | 10-2018-0096947 A | 8/2018 | |
| TW | 92112990 | 5/2003 | |
| WO | 88/00235 | 1/1988 | |
| WO | 99/31222 | 6/1999 | |
| WO | 2006/041429 A2 | 4/2006 | |
| WO | 2014/036187 A1 | 3/2014 | |
| WO | WO 2014/141136 A1 | 9/2014 | |
| WO | 2015/073918 A1 | 5/2015 | |
| WO | 2017/019970 A1 | 2/2017 | |
| WO | 2018/011805 A2 | 1/2018 | |
| WO | 2019/014652 A1 | 1/2019 | |
| WO | 2019/122239 A1 | 6/2019 | |
| WO | 2020/243324 A1 | 12/2020 | |
| WO | 2021/102375 A1 | 5/2021 | |
| WO | 2021/108093 A1 | 6/2021 | |
| WO | 2021/108094 A1 | 6/2021 | |
| WO | WO-2022036371 A1 * | 2/2022 | ............. A23L 13/00 |

OTHER PUBLICATIONS

Office Action as received in Canadian application 3,219,264 dated Sep. 18, 2024.

Office Action as received in Mexican application MX/a/2022/006095 dated Oct. 4, 2024.

Search Report and Written Opinion as received in SG Application No. 10202402267S dated Oct. 15, 2024.

U.S. Appl. No. 18/439,503 filed Oct. 11, 2024.

Examination Report as received in Australian application 2022203772 dated Feb. 28, 2024.

Office Action as received in Japanese application 2024-045237 dated May 29, 2024.

(56)                References Cited

OTHER PUBLICATIONS

Examination Report as received in Australian application 2023200307 dated Jun. 21, 2024.
Examination Report as received in Australian application 2022203772 dated Jun. 24, 2024.
Office Action as received in KR application 10-2024-7009465 dated Jun. 25, 2024.
Notice of Eligibility for Grant and Examination Report as received in SG application 11202113006V dated Jul. 1, 2024.
U.S. Appl. No. 18/439,503, May 29, 2024, Office Action.
Examination Report as received in Australian application 2023200307 dated Feb. 7, 2025.
EPO Communication pursuant to Article 94(3) as received in application 20834000.0 dated Dec. 3, 2024.
Notice of Allowance as received in JP application 2024-045237 dated Jan. 17, 2025.
Notice of Allowance as received in KR application 10-2024-7009465 dated Dec. 13, 2024.
Search Report as received in Taiwanese application 113101738 dated Dec. 23, 2024.
U.S. Appl. No. 17/558,243, Jan. 14, 2025, Office Action.
International Search Report and Written Opinion mailed on Nov. 9, 2020, in International Application No. PCT/US2020/034949, 15 pages.
International Search Report and Written Opinion mailed on Mar. 12, 2021, in International Application No. PCT/US2020/061676, 13 pages.
International Search Report & Written Opinion as received in PCT/US 22/78310 dated Feb. 21, 2023.
Acevedo et al., "Micropatterning Technology to Design an Edible Film for In Vitro Meat Production", Food and Bioprocess Technology, vol. 11, No. 7, Mar. 25, 2018, pp. 1267-1273.
Bhat et al., Prospectus of cultured meat-advancing meat alternatives, Journal of Food Science and Technology, vol. 48, No. 2, Dec. 30, 2010, pp. 125-140.
Brunette, "Fibroblasts on micromachined substrata orient hierarchically to grooves of different dimensions," Exp Cell Res. 1986; 164(1):11-26.
Brunette, "Spreading and orientation of epithelial cells on grooved substrata," Exp Cell Res. 1986; 167(1):203-217.
Clark et al., "Topographical control of cell behaviour: II. multiple grooved substrata," Development 108, 635-644 (1990).
Datar et al., "Possibilities for an in vitro meat production system," Innovative Food Science and Emerging Technologies, vol. 11, No. 1, Jan. 1, 2010, pp. 13-22.
Gaydhane et al., "Cultured meat: state of the art and future," Biomanufacturing Reviews, vol. 3, No. 1, Mar. 19, 2018.
Karuri et al., "Biological length scale topography enhances cell-substratum adhesion of human corneal epithelial cells," J Cell Sci. 2004; 117: 3153-3164.
Lam et al., "Microfeature guided skeletal muscle tissue engineering for highly organized 3-dimensional free-standing constructs", Biomaterials, vol. 30, No. 6, Feb. 1, 2009, pp. 1150-1155.
Ostrovidov et al., "Skeletal Muscle Tissue Engineering: Methods to Form Skeletal Myotubes and Their Applications" Tissue Engineering: Part B, vol. 20, No. 5, Oct. 1, 2014 (Oct. 1, 2014), pp. 403-436.
Riboldi et al., "Electrospun degradable polyesterurethane membranes: potential scaffolds for skeletal muscle tissue engineering," Biomaterials, vol. 26, No. 22, 1August 2005, pp. 4606-4615.
Hosseini et al. "Engineered contractile skeletal muscle tissue on a microgrooved methacrylated gelatin substrate." Tissue Eng Part A. Dec. 2012;18(23-24):2453-65. (Year: 2012).
Bajaj et al. "Patterning the differentiation of C2C12 skeletal nnyoblasts." Integrative Biology, vol. 3, Issue 9, Sep. 2011, pp. 897-909 (Year: 2011).
Cha et al. "Study of myoblast differentiation using multi-dimensional scaffolds consisting of nano and micropatterns." Biomater Res .Jan. 11, 2017;21:1. (Year: 2017).

Charest et al. "Myoblast alignment and differentiation on cell culture substrates with microscale topography and model chemistries." Biomaterials.Apr. 2007;28(13):2202-10. (Year: 2007).
Zeng et al. "A minimally invasive method for retrieving single adherent cells of different types from cultures", Sci Rep .Jun. 24, 2014;4:5424. (Year: 2014).
Willem Visser et al. "Quantifying Cell Adhesion through Impingement of a Controlled Microjet."Biophys J. Jan. 6, 2015; 108(1): 23-31. (Year: 2015).
"What is Fluid Mechanics." Mechanical Engineering. Penn State College of Engineering. Retrieved on Dec. 1, 2021. Retrieved from https://www.rne.psu.eduicinnbala/Learning/Fluid/Introductory/ what is fluid rnechanics.htm (Year: 2021).
Examination Report as received in Australian application 2020284005 dated May 2, 2022.
Examination Report as received in Australian application 2022241490 dated Nov. 3, 2022.
Examination Report as received in Australian application 2022241490 dated Jan. 25, 2023.
Office Action as received in Canadian application 3,141,870 dated Jun. 3, 2022.
Office Action as received in Canadian application 3,160,109 dated Sep. 15, 2022.
Notice of Allowance as received in Canadian application 3,201,964 dated Jul. 18, 2023.
Notice of Allowance as received in Canadian application 3,201,964 dated Aug. 30, 2023.
Notice of Allowance as received in CA application 3,210,518 dated Nov. 21, 2023.
Conditional Notice of Allowance as received in Canadian application 3,198,589 dated Sep. 5, 2023.
Office Action as received in Chinese application 202080080154.X dated Jan. 3, 2023.
Office Action as received in Chinese application 202080080154.X dated May 7, 2023.
Office Action as received in CN application 202080080154.X dated Nov. 7, 2023.
Office Action as received in Chinese application 202080049214.1 dated Jul. 15, 2022 [No English translation available].
Office Action as received in Chinese application 202080049214.1 dated Jan. 20, 2023 [No English translation available].
Office Action as received in Chinese application 202080049214.1 dated May 16, 2023.
Office Action as received in Chinese application 2023116995466 dated Apr. 25, 2024.
Office Action as received in Chinese application 2023117065159 dated Apr. 15, 2024.
EPO Communication pursuant to Article 94(3) as received in application 20745342.4 dated Feb. 28, 2024.
Office Action as received in European application 20745342.4 dated Dec. 9, 2021.
Office Action as received in European application 20834000.0 dated Jun. 10, 2022.
Office Action as received in Japanese application 2022-525657 dated Oct. 31, 2022 [No English translation available].
Office Action as received in Japanese application 2022-525657 dated Apr. 21, 2022.
Notice of Allowance as received in Japanese application 2022-525657 dated Jul. 24, 2023.
Office Action as received in JP application 2023-133508 dated Oct. 27, 2023.
Notice of Allowance as received in JP application 2023-133508 dated Feb. 26, 2024.
Office Action as received in Israeli application 288338 dated May 25, 2022.
Office Action as received in Israeli application 296327 dated Mar. 23, 2023.
Notice of Allowance as received in IL application 304043 dated Dec. 12, 2023.
Office Action as received in IL application 304041 dated Nov. 27, 2023.
Office Action as received in Korean application 10-2022-7015187 dated Nov. 1, 2022.

(56)                    References Cited

OTHER PUBLICATIONS

Office Action as received in KR application 10-2023-7020481 dated Sep. 26, 2023.
Notice of Allowance as received in KR application 10-2022-7015187 dated Apr. 14, 2023.
Notice of Allowance as received in KR application 10-2023-7020481 dated Jan. 18, 2024.
Office Action as received in Mexican application MX/a/2022/006095 dated Jun. 1, 2022 [No English translation available].
Office Action as received in Mexican application MX/a/2022/006095 dated Apr. 5, 2024.
Notice of Allowance as received in Philippines application 1-2022-550989 dated Dec. 7, 2023.
Search Report and Written Opinion as received in SG application 11202113006V dated Dec. 4, 2023.
Office Action as received in Taiwanese application 109117927 dated Jan. 9, 2023.
Notice of Allowance as received in Taiwanese application 109117927 dated Oct. 12, 2023.
Office Action as received in Thailand application 2201002725 dated Apr. 24, 2023.
Search Report and Written Opinion as received in SG Application No. 11202203957S dated Feb. 7, 2024.
U.S. Appl. No. 17/131,514, Mar. 3, 2021, Office Action.
U.S. Appl. No. 17/131,514, Jun. 16, 2021, Office Action.
U.S. Appl. No. 17/131,514, Dec. 6, 2021, Office Action.
U.S. Appl. No. 17/131,514, Mar. 29, 2022, Notice of Allowance.
U.S. Appl. No. 17/100,705, Apr. 21, 2021, Office Action.
U.S. Appl. No. 17/100,705, Aug. 10, 2021, Notice of Allowance.
U.S. Appl. No. 17/469,687, Apr. 13, 2022, Notice of Allowance.
U.S. Appl. No. 17/469,680, Apr. 15, 2022, Office Action.
U.S. Appl. No. 17/469,680, Jul. 15, 2022, Notice of Allowance.
U.S. Appl. No. 17/812,315, Oct. 31, 2022, Office Action.
U.S. Appl. No. 17/812,315, Feb. 1, 2023, Notice of Allowance.
U.S. Appl. No. 17/660,165, Jul. 18, 2022, Office Action.
U.S. Appl. No. 17/660,165, Nov. 3, 2022, Notice of Allowance.
U.S. Appl. No. 17/660,170, Jul. 21, 2022, Office Action.
U.S. Appl. No. 17/660,170, Nov. 8, 2022, Notice of Allowance.
U.S. Appl. No. 18/047,196, Jan. 27, 2023, Office Action.
U.S. Appl. No. 18/047,196, May 10, 2023, Office Action.
U.S. Appl. No. 18/047,196, Oct. 13, 2023, Office Action.
U.S. Appl. No. 18/047,196, Feb. 22, 2024, Office Action.
U.S. Appl. No. 18/047,196, Mar. 29, 2024, Notice of Allowance.
U.S. Appl. No. 18/047,545, Feb. 9, 2023, Office Action.
U.S. Appl. No. 18/047,545, May 23, 2023, Office Action.
U.S. Appl. No. 18/047,545, Oct. 12, 2023, Office Action.
U.S. Appl. No. 18/047,545, Feb. 22, 2024, Office Action.
U.S. Appl. No. 18/047,545, Apr. 4, 2024, Notice of Allowance.

Notice of Acceptance as received in Australian application 2020284005 dated Aug. 29, 2024.
Office Action as received in Chinese application 2023116995466 dated Aug. 17, 2024.
Office Action as received in Chinese application 2023117065159 dated Aug. 21, 2024.
Notice of Allowance as received in IL application 304041 dated Aug. 1, 2024.
Lam et al: "The effect of continuous wavy micropatterns on silicone substrates on the alignment of skeletal muscle myoblasts and myotubes", Biomaterials, Elsevier, Amsterdam, NL, vol. 27, No. 24, Aug. 1, 2006 (Aug. 1, 2006), pp. 4340-4347, XP005430415, ISSN: 0142-9612, DOI: 10.1016/J.BIOMATERIALS.2006.04.012.
EPO Communication pursuant to Article 94(3) as received in application 20745342.4 dated Mar. 7, 2025.
Notice of Allowance as received in IL application 319980 dated May 20, 2025.
Notice of Allowance as received in Mexican application MX/a/2022/006095 dated May 14, 2025.
Examination Report and Notice of Eligibility for Grant as received in SG Application No. 11202203957S dated Jul. 14, 2025.
Examination Report as received in Australian application 2023200307 dated Jun. 16, 2025.
Notice of Acceptance as received in Australian application 2023200307 dated Jun. 17, 2025.
Second Office Action received in Canadian application 3,219,264 dated Jun. 26, 2025.
Notice of Allowance as received in IL application 310833 dated Jun. 15, 2025.
Notice of Allowance as received in IL application 321803 dated Aug. 12, 2025.
U.S. Appl. No. 17/558,243, Jun. 30, 2025, Office Action.
Examination Report and received in Canadian application 3,229,492 dated Aug. 7, 2025.
Examination Report as received in Australian application 2023200307 dated Sep. 26, 2025.
Examination Report as received in Australian application 2023200307 dated Feb. 16, 2026.
Office Action as received in IL application 323083 dated Jan. 22, 2026.
Office Action as received in IL application 323927 dated Mar. 16, 2026.
Notice of Eligibility for Grant and Examination Report as received in SG application 11202502130U dated Mar. 4, 2026.
Written Opinion as received in SG Application No. 10202402267S dated Mar. 31, 2026.
U.S. Appl. No. 17/558,243, Jan. 14, 2026, Office Action.
U.S. Appl. No. 18/060,322, Mar. 30, 2026, Office Action.

* cited by examiner

502

506

504

500a

512

514

500b

Arrange One Or More Cell Culture Substrates *1202*

Contact Cells To A Surface Of The Substrate *1204*

Grow Cells On The Substrate *1206*

Detach Cell Sheet From The Substrate *1208*

Comestible Cell-Based Meat Product *1210*

2100

Flowing Cells Into An Elongated Bioreactor 2102

Arresting Flow To Allow Cells To Settle And Adhere To Substrates Of The Elongated Bioreactor 2104

Circulating Cell Culture Media Through The Elongated Bioreactor At An Increasing Flow Rate To Reduce Shearing Of Cells While Promoting Growth 2106

2200

Growing Cells Within A Plurality Of Interconnected Elongated Bioreactors
2202

Closing Valves To Bioreactors Other Than At Least One Bioreactor Of The Plurality Of Interconnected Elongated Bioreactors 2204

Harvesting Cells From The At Least One Bioreactor 2206

Cleaning The At Least One Bioreactor In Place By Flowing Fluid Therethrough 2208

METHODS OF USING PIPE-BASED BIOREACTORS FOR PRODUCING COMESTIBLE MEAT PRODUCTS

CROSS-REFERENCE TO RELATED APPLICATIONS

This application is a continuation of U.S. patent application Ser. No. 18/047,545, filed Oct. 18, 2022, which is a continuation of U.S. patent application Ser. No. 18/047,196, filed Oct. 17, 2022. Each of the aforementioned applications is hereby incorporated by reference in its entirety.

BACKGROUND

As the world's population continues to grow, cell-based or cultured meat products for consumption have emerged as an attractive alternative (or supplement) to conventional meat from slaughtered animals. For instance, cell-based, cultivated, or cultured meat represents a technology that could address the specific dietary needs of humans. Cell-based meat products can be prepared from a combination of cultivated adherent and suspension cells derived from a non-human animal.

In addition to addressing dietary needs, cell-based meat products help alleviate several drawbacks linked to conventional meat products for humans, livestock, and the environment. For instance, conventional meat production involves controversial practices associated with animal husbandry and slaughter. Other drawbacks associated with slaughtered meat production include low conversion of caloric input to edible nutrients, microbial contamination of the product, emergence and propagation of veterinary and zoonotic diseases, relative natural resource requirements, and resultant industrial pollutants, such as greenhouse gas emissions and nitrogen waste streams.

Despite advances in creating cell-based meat products, existing methods for cultivating and processing cell-based meat products face several shortcomings. In particular, existing methods for cultivating and processing cell-based meat products often suffer from slow cellular growth and lack of cellular tissue mass. Existing methods for cultivating cell-based meat products are often costly in terms of both time and processing resources. More specifically, existing methods require prohibitive amounts of time to generate small amounts of cell-based meat products. For instance, existing methods often take eleven or more days to form a thin layer of cell-based tissue. To compensate for slow times of growing cell-based tissue and the lack of cellular tissue mass, some existing manufacturers ramp up the same existing methods by increasing the number and size of machines and tools used to grow cellular tissue. However, such upscaling of cultivation equipment presents additional challenges with respect to overall equipment and supply costs, sterility and cleanability of bioreactors and support equipment, and harvestability of cultivated cells. Relatedly, many conventional systems, particularly when upscaled for increased production, limit the operability of ideal flow rates, flow distribution, and heat and mass transfer during cultivation processes.

These, along with additional problems and issues are present in existing methods, apparatuses, and systems for cultivating cell-based meat products.

BRIEF SUMMARY

Embodiments of the present disclosure provide benefits and/or solve one or more of the foregoing or other problems in the art with systems, apparatuses, and methods for preparing a comestible cell-based meat product utilizing one or more pipe-based bioreactors. In one or more embodiments, for example, the one or more pipe-based bioreactors comprise a plurality of substrates conforming to an interior profile of an elongated cylindrical enclosure. Cells may be injected into the one or more pipe-based bioreactors, where they adhere to the plurality of substrates and are cultivated thereon to form cell-based meat products. In some embodiments, each pipe-based bioreactor in a system of pipe-based bioreactors can be cleaned, seeded, cultivated, and/or harvested independently—without disrupting other pipe-based bioreactors in the system.

Also, the disclosed embodiments include systems, apparatuses, and methods providing additional advantages over existing solutions, such as improved flow control during steaming, cleaning, seeding, cultivating, and/or harvesting processes. Further, one or more embodiments enable seeding on both sides of planar substrates for increased yield of cell-based meat products. In some embodiments, multiple pipe-based bioreactors are interconnected (e.g., arranged in parallel) within a system comprising shared sources of steam, cell culture, nutrients, and so forth. Also, in some embodiments, pipe-based bioreactors are mounted at an angle with offset inlets and outlets to reduce accumulation of condensation (i.e., pooling) during steaming and to reduce accumulation of gas bubbles during inoculation and cultivation. Accordingly, the disclosed embodiments present various improvements in cost of manufacture and process efficiency.

Additional features and advantages of one or more embodiments of the present disclosure are outlined in the description which follows, and in part will be obvious from the description, or may be learned by the practice of such example embodiments.

BRIEF DESCRIPTION OF THE DRAWINGS

The detailed description provides one or more embodiments with additional specificity and detail through the use of the accompanying drawings, as briefly described below.

3

Figure 10:
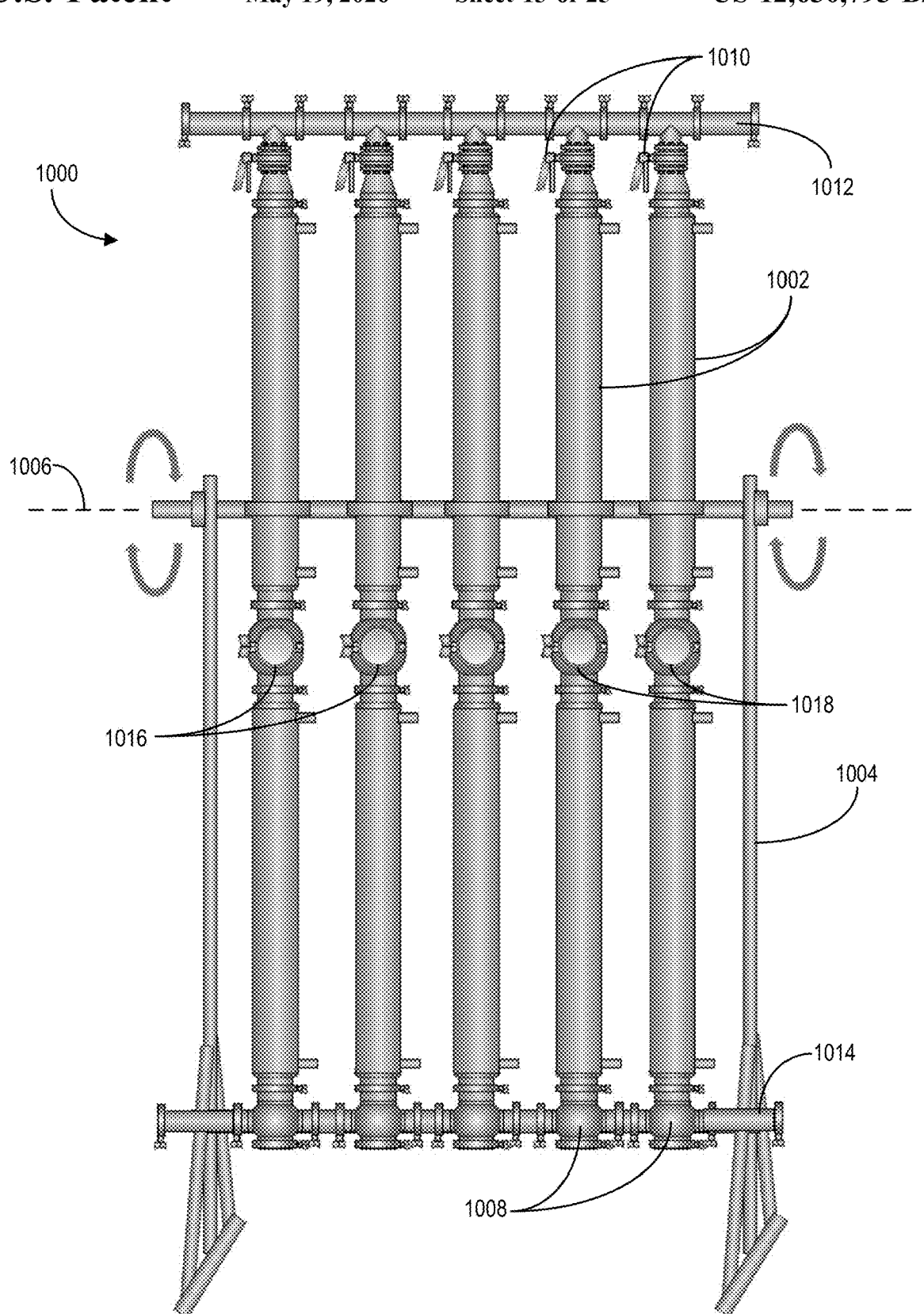

FIG. 10 illustrates a rotatable series of interconnected pipe-based bioreactors in accordance with one or more embodiments.

Figure 11:
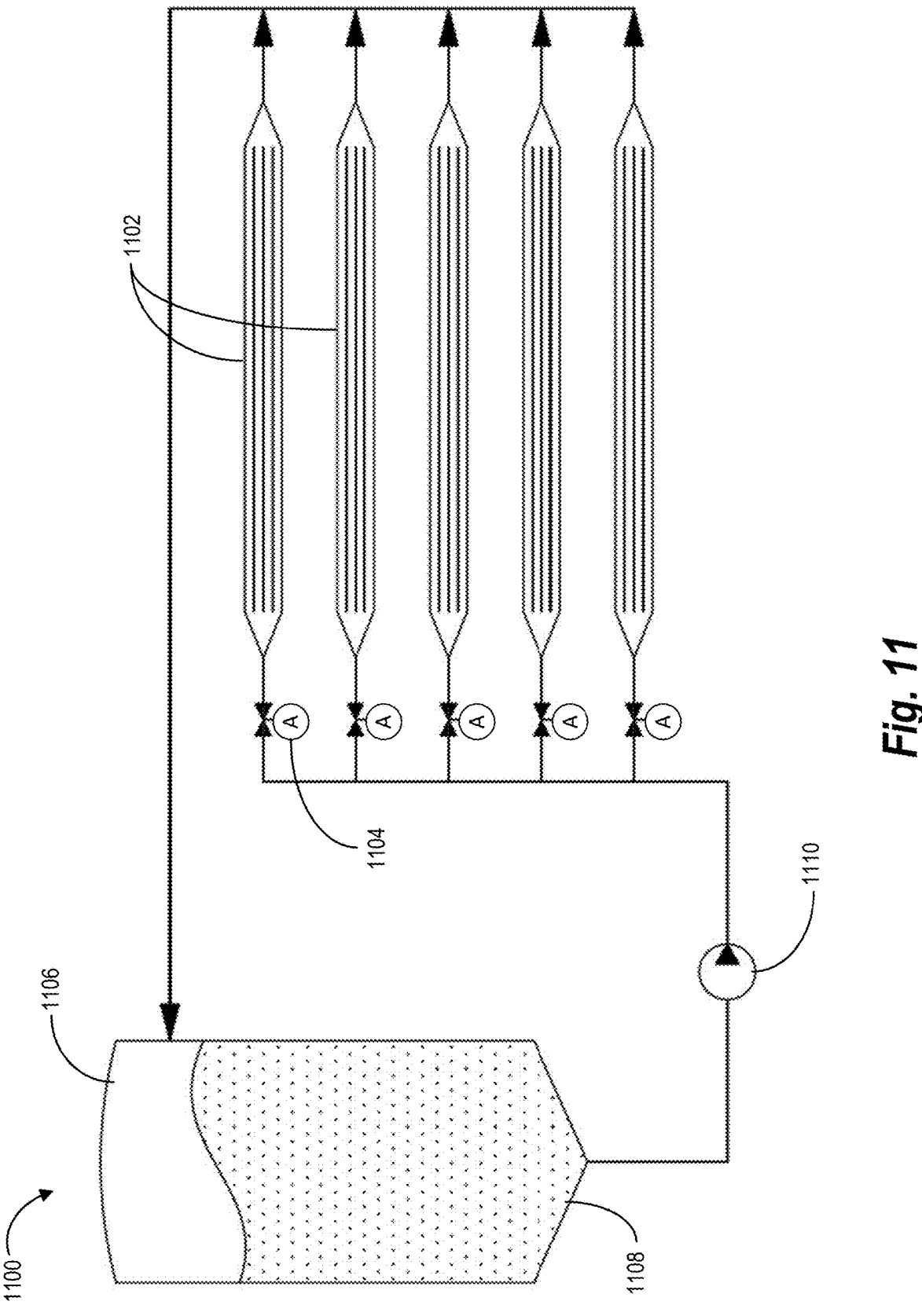

FIG. 11 illustrates a system of interconnected pipe-based bioreactors in accordance with one or more embodiments.

Figure 12:
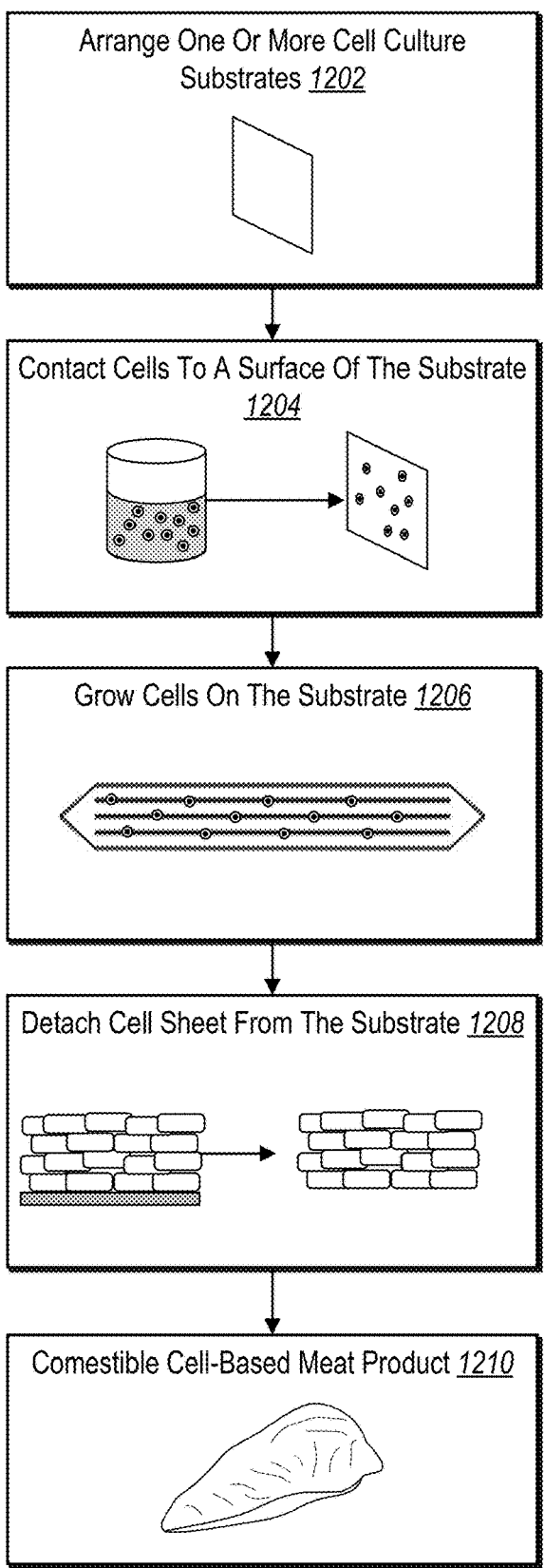

FIG. 12 illustrates a flowchart of a series of acts for preparing a comestible cell-based meat product in accordance with one or more embodiments.

Figure 13:
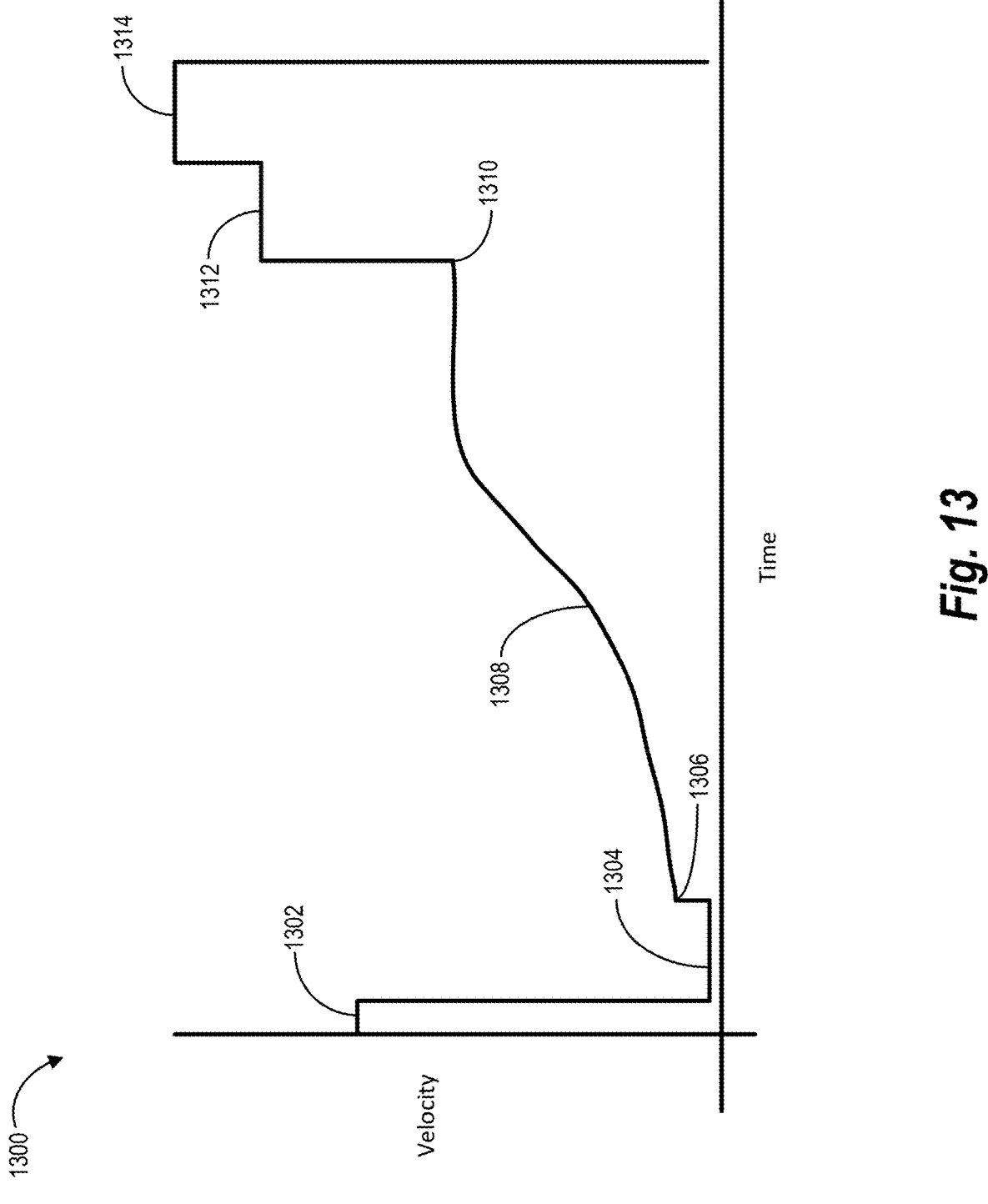

FIG. 13 illustrates a graph of a series of acts for preparing a comestible cell-based meat product in accordance with one or more embodiments.

Figure 14:
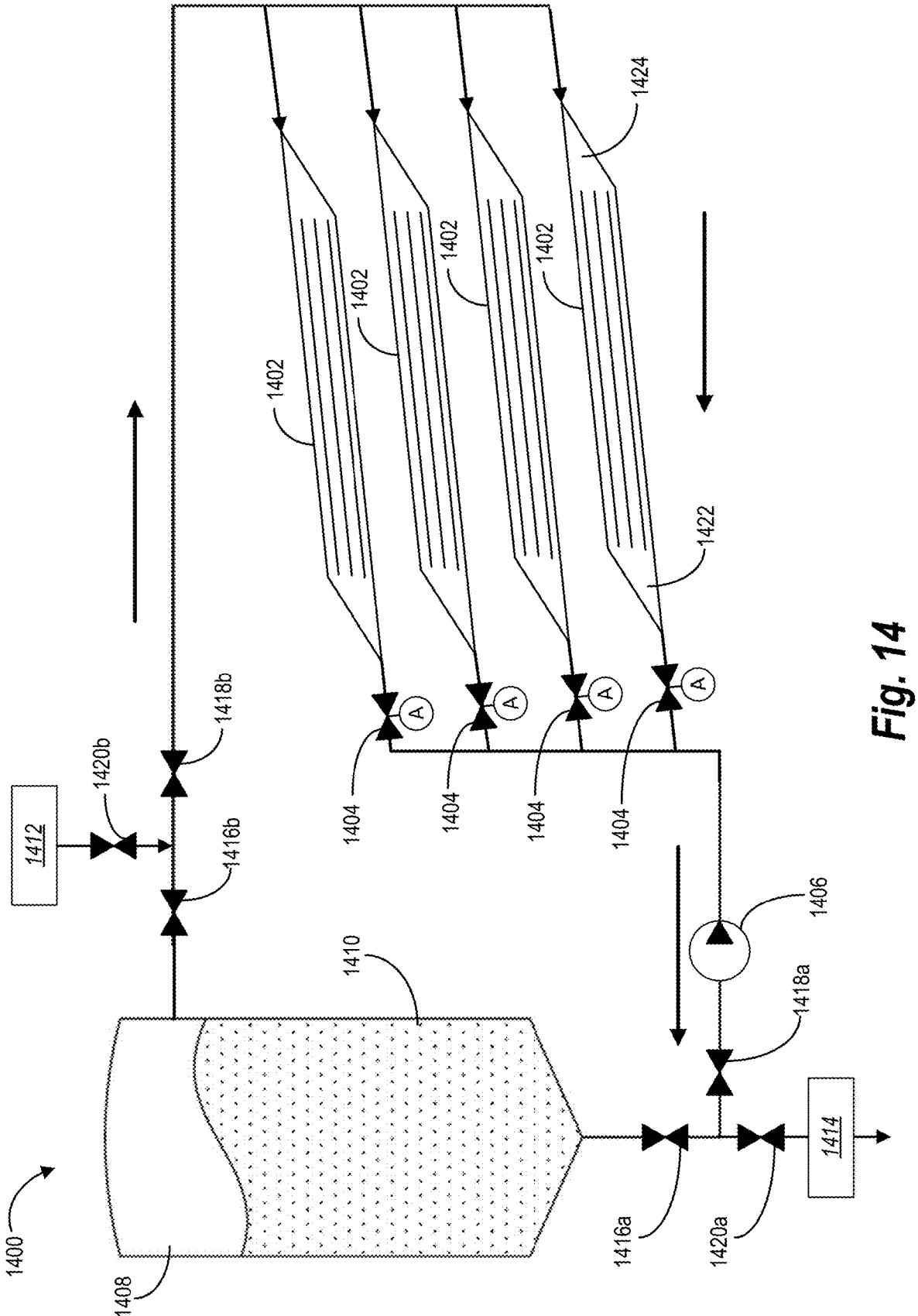

FIG. 14 illustrates a method for steaming a system of interconnected pipe-based bioreactors in accordance with one or more embodiments.

Figure 15:
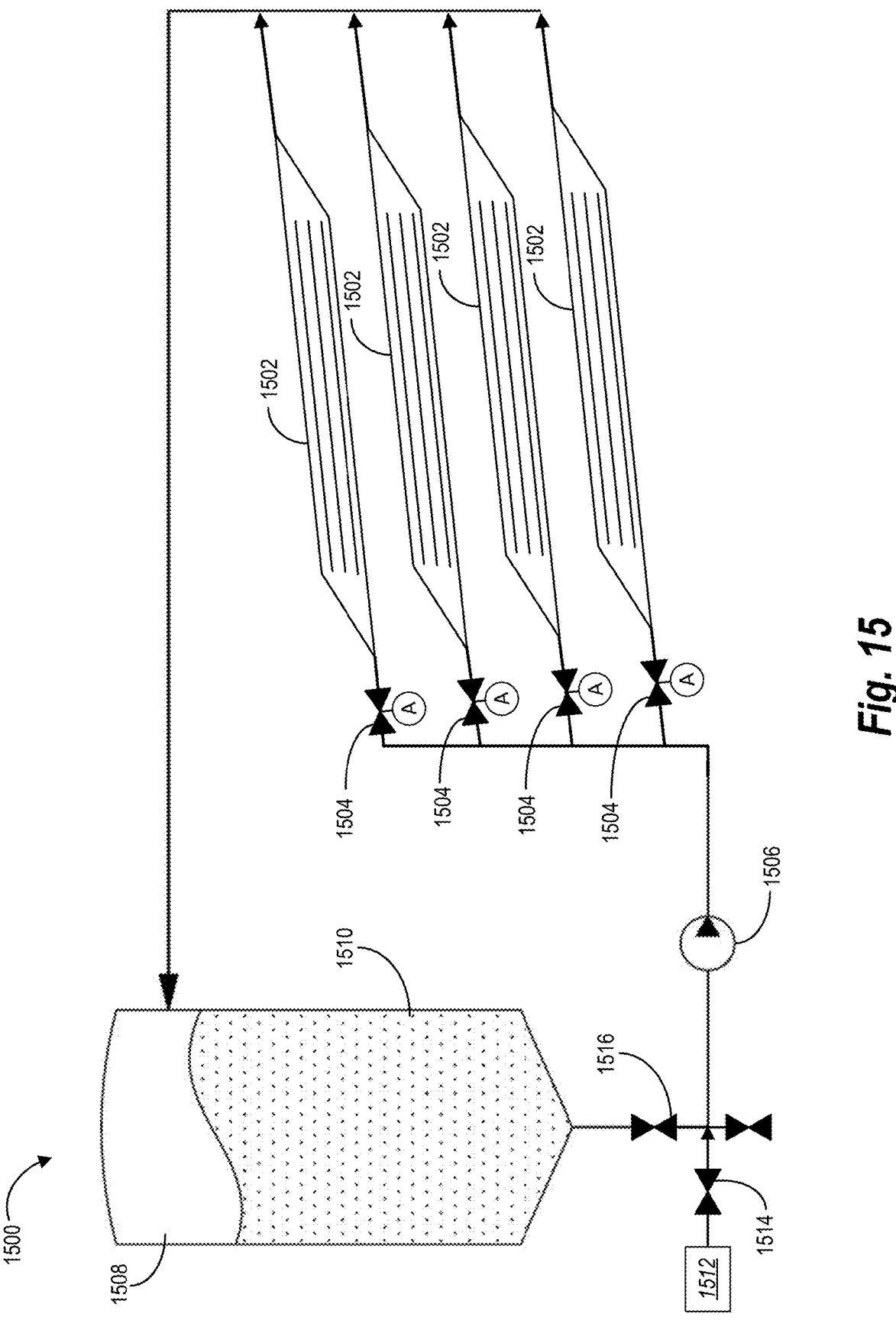

FIG. 15 illustrates a method for inoculating a system of interconnected pipe-based bioreactors in accordance with one or more embodiments.

Figure 16:
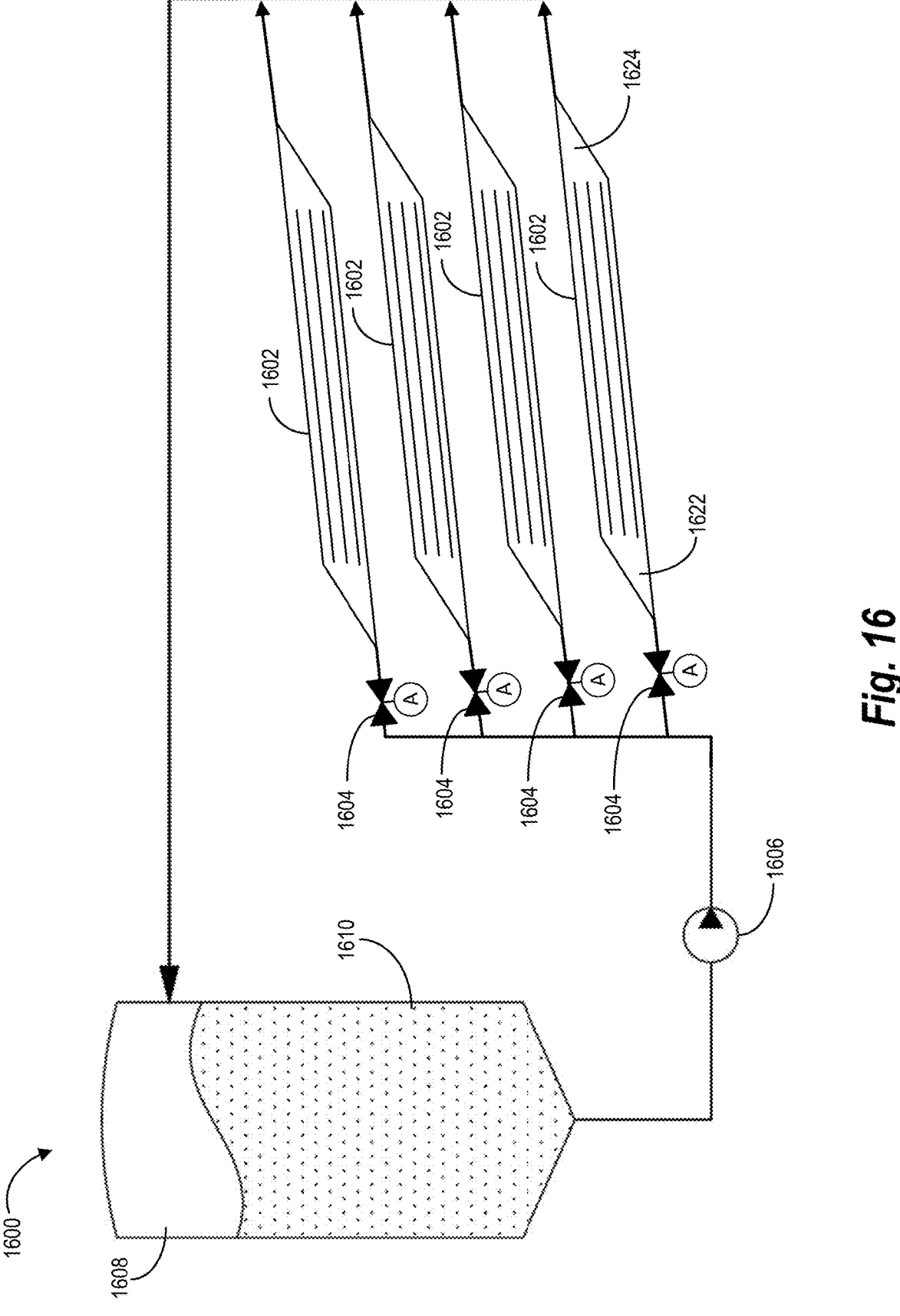

FIG. 16 illustrates a method for cultivating cells within a system of interconnected pipe-based bioreactors in accordance with one or more embodiments.

Figure 17:
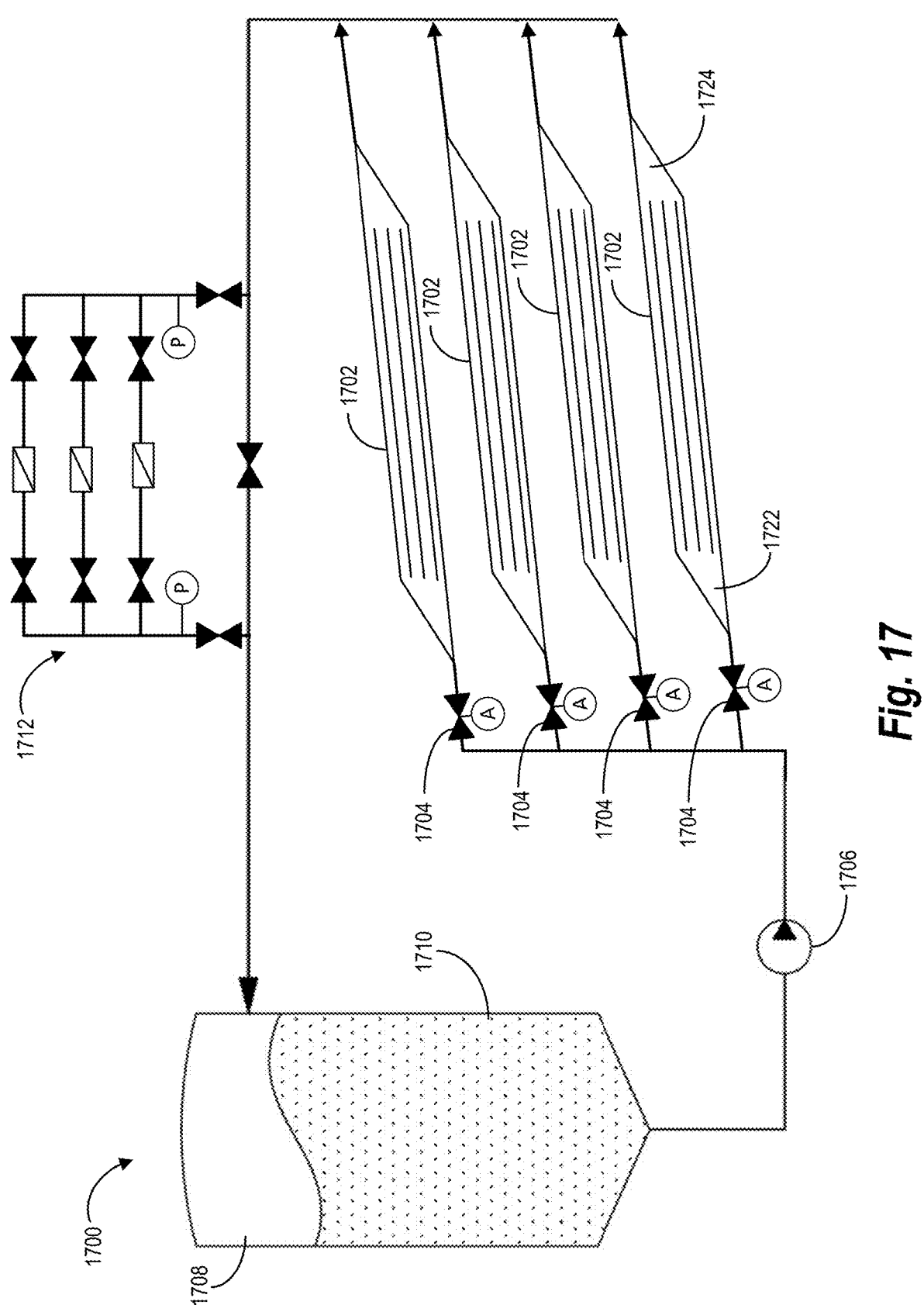

FIG. 17 illustrates a method for harvesting cells from a system of interconnected pipe-based bioreactors in accordance with one or more embodiments.

Figure 18:
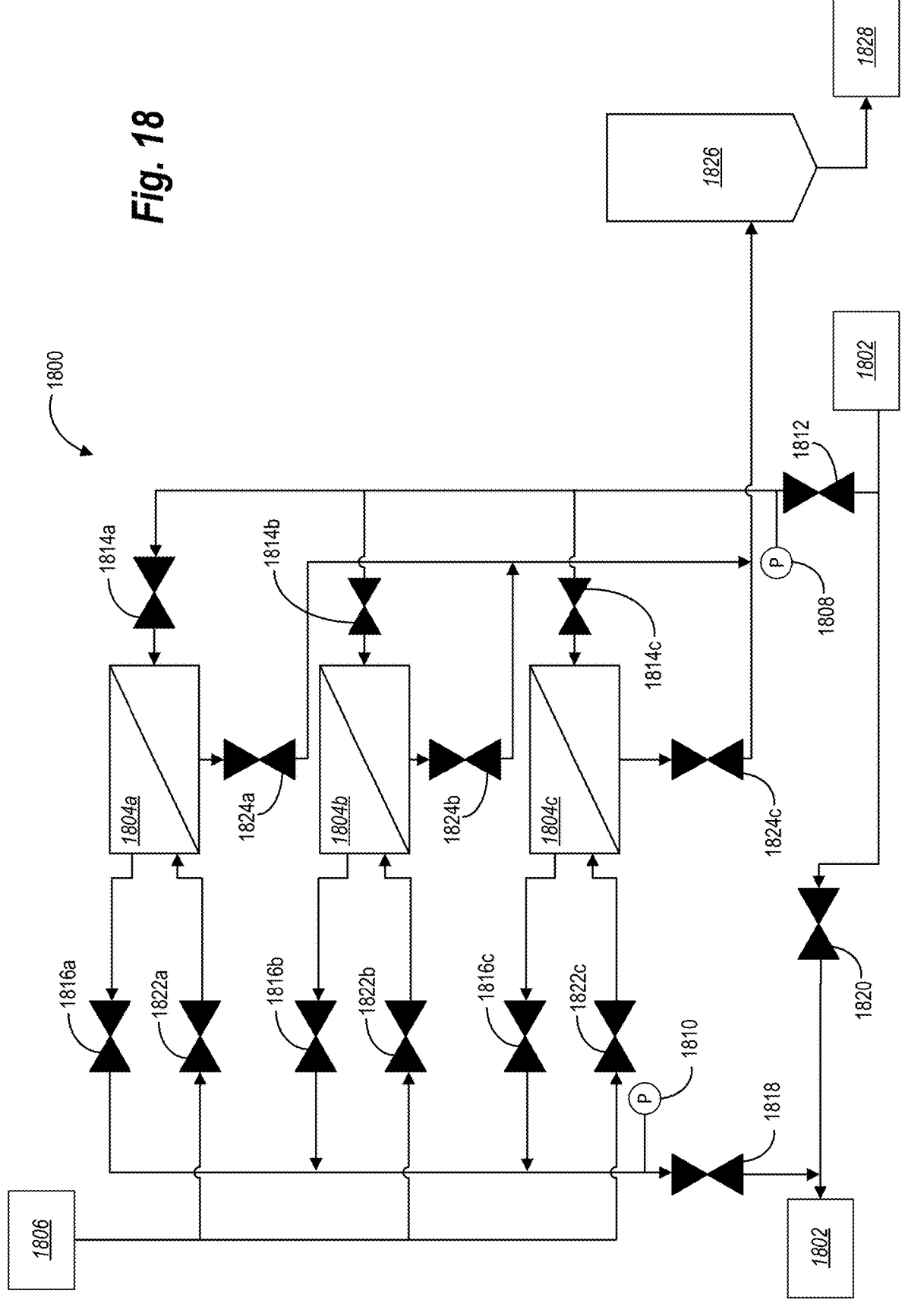

FIG. 18 illustrates a harvester mechanism in accordance with one or more embodiments.

Figure 19:
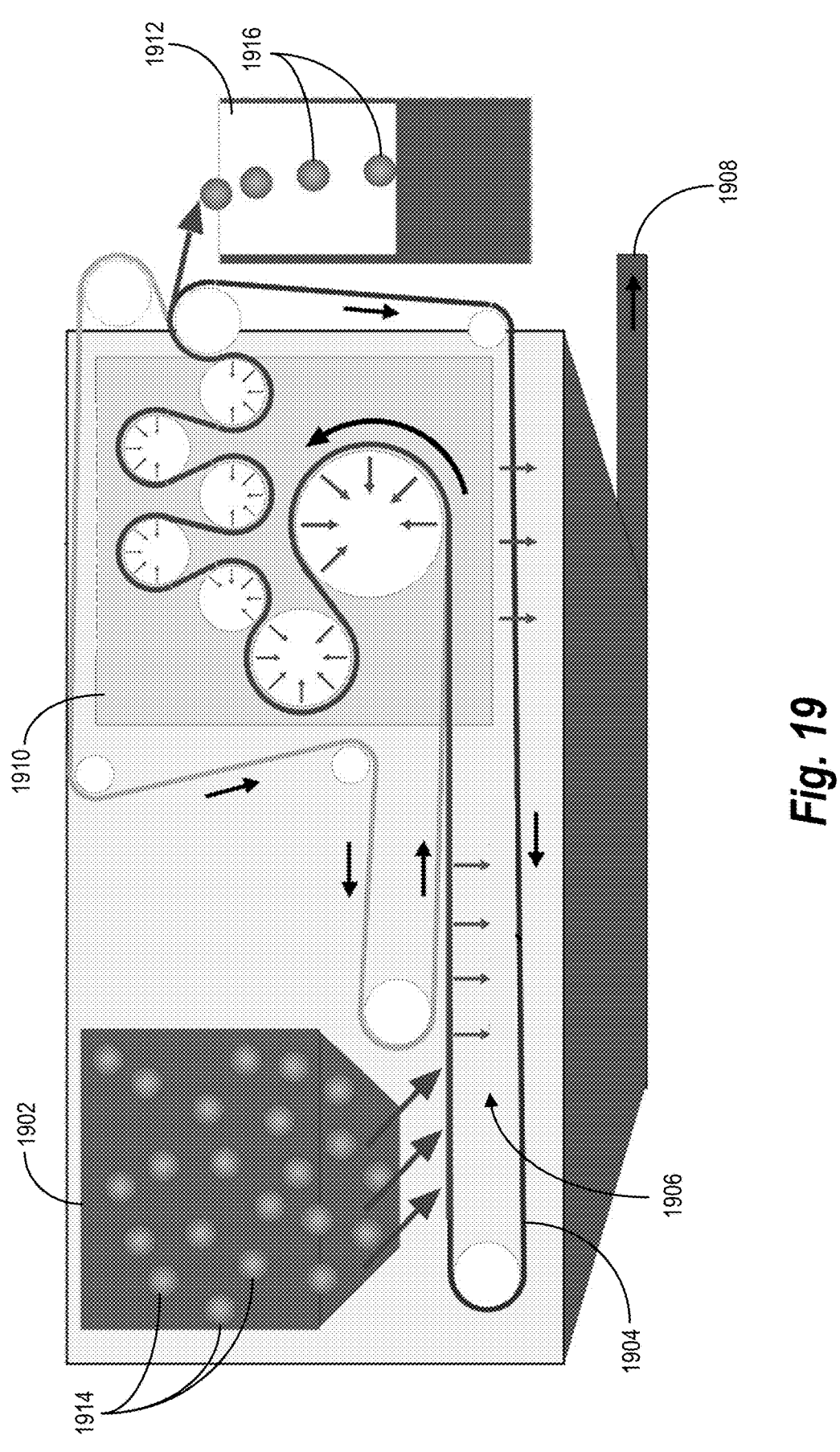

FIG. 19 illustrates a belt filter for collecting and processing meat cells in accordance with one or more embodiments.

Figure 20:
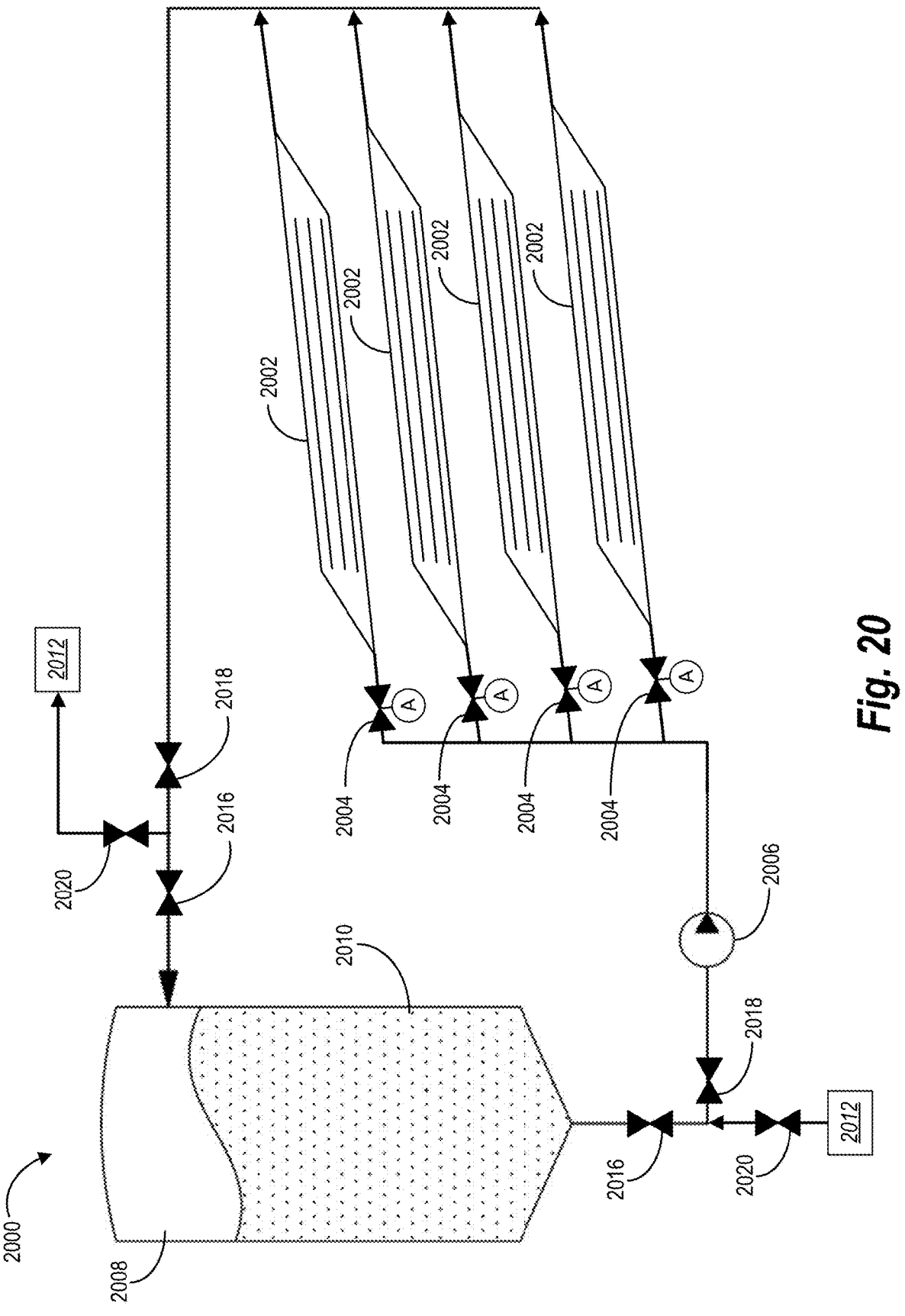

FIG. 20 illustrates a method for cleaning a system of pipe-based bioreactors in accordance with one or more embodiments.

Figure 21:
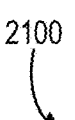
Figure 21:
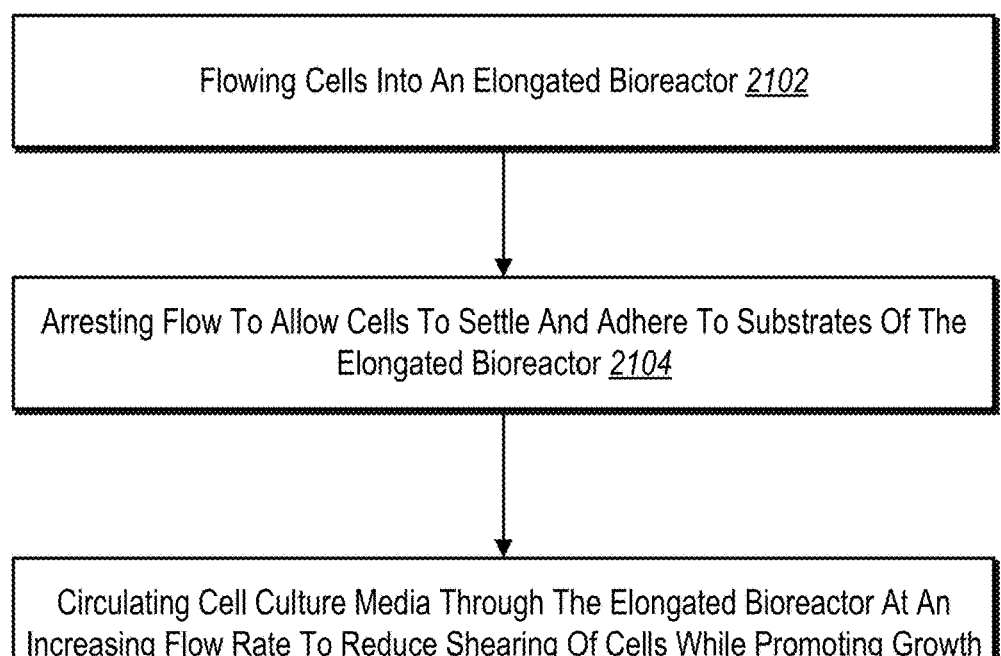
Figure 22:
Figure 22:
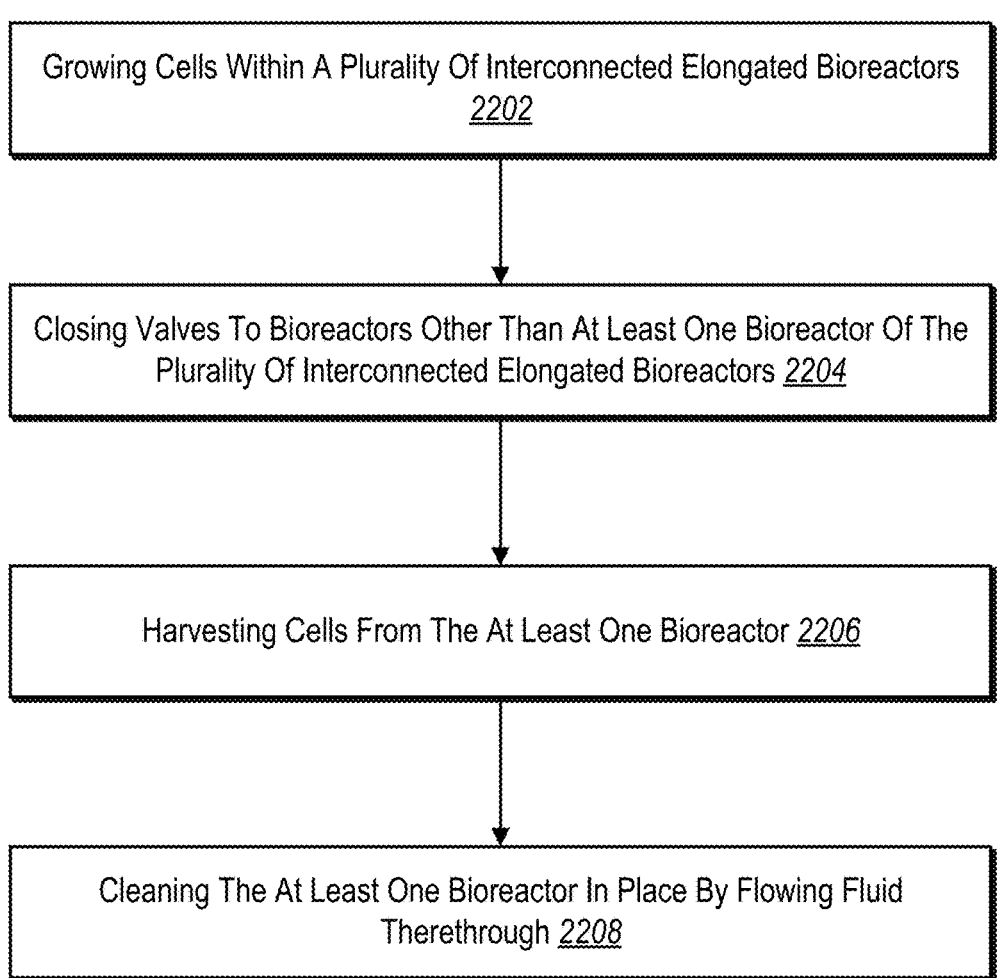

FIGS. 21-22 illustrate flowcharts of two series of acts for preparing comestible meat products in accordance with one or more embodiments.

DETAILED DESCRIPTION

This disclosure describes one or more embodiments of a pipe-based bioreactor for preparing comestible cell-based meat products and methods of using the same. To illustrate, the comestible cell-based meat products generally contain cultured animal tissues prepared by adhering cells derived from a non-human animal to one or more substrates within an enclosed bioreactor, cultivating the cells with a cell culture media to promote cell growth, and harvesting the cell-based meat product by detaching the cultured cells from the one or more substrates. In particular, the disclosed embodiments include pipe-based bioreactors comprising one or more substrates disposed within an elongated enclosure and various methods for using pipe-based bioreactors to prepare comestible cell-based meat products. In some embodiments, a pipe-based bioreactor includes a plurality of parallel stacked planar substrates conforming to an interior profile of the elongated enclosure. In some examples, the substrates are not strictly planar, but instead substantially planar. For instance, the substrate may be substantially planar and include indents or ridges for spacing and strength as described below.

In some embodiments, for example, a pipe-based bioreactor for preparing a comestible meat product includes an elongated cylindrical enclosure defining a cavity, and a plurality of nominally spaced substrates arranged within the cavity. Also, in one or more embodiments, the plurality of nominally spaced substrates conforms to an interior profile of the elongated cylindrical enclosure and is configured to support growth of the comestible meat product. As disclosed herein, pipe-based bioreactors enable higher fluid velocities, improved flow distribution, improved temperature distribution, and lower overall costs in comparison to conventional systems.

Moreover, as disclosed herein, pipe-based bioreactors enable improved control of internal conditions during each process of the production of comestible meat products. For example, as disclosed herein, the increased fluid velocities enabled by a pipe-based bioreactor of relatively small diameter increases shear forces on cultured cells within the bioreactor when harvesting meat product by flowing fluid at an elevated flow rate to remove the cultured cells. Also, the disclosed embodiments enable improved control and implementation of ideal conditions within bioreactors for cleaning, such as improved control and consistency of PH levels, temperatures, and duration of contact with cleaning solutions within the pipe-based bioreactor. Moreover, in some implementations, the foregoing improvements enable increased efficiency of production relative to conventional systems.

Moreover, in some embodiments, a pipe-based bioreactor is mounted to a ground surface at an acute angle relative to the ground surface, such that the pipe-based bioreactor and the one or more substrates disposed therein are at an incline. As disclosed herein, the inclined pipe-based bioreactor prevents accumulation of fluid condensation (i.e., pooling) during steaming (or cleaning) of the pipe-based bioreactor as the fluid flows with gravity down the incline and out of the pipe-based bioreactor. Also, the inclined pipe-based bioreactor prevents the accumulation of gas bubbles during the cultivation process as the buoyancy of the gas bubbles causes them to rise up the incline and out of the pipe-based bioreactor.

Additionally, in one or more embodiments, a system for preparing a comestible meat product includes a plurality of interconnected pipe-based bioreactors coupled to one or more fluid sources, such as sources of steam, culture media, cleaning chemicals, and other fluids necessary for the preparation of cell-based meat products. In some embodiments, the system of pipe-based bioreactors includes a plurality of valves for selectively opening and closing connections between the pipe-based bioreactors and the one or more fluid sources, such that each pipe-based bioreactor can be operated individually. For instance, each pipe-based bioreactor within the system can be selectively and individually cleaned, seeded with cells, cultivated with cell culture media, and harvested to remove cultured cells therefrom without disrupting other pipe-based bioreactors within the system. In addition, the one or more fluid sources can be cleaned, repaired, or otherwise maintained without disrupting the plurality of pipe-based bioreactors. Moreover, by enabling selective operation of each interconnected pipe-based bioreactor within a bioreactor system, the disclosed embodiments allow for reduced resources, such as fluid sources and/or pumps.

As mentioned above, the disclosed embodiments enable improved flow distribution and higher fluid velocities during procedures for preparing cell-based meat products. For example, in some embodiments, a method for producing a comestible meat product includes flowing cells into an elongated bioreactor (e.g., a pipe-based bioreactor according to one or more disclosed embodiments) for a first period of time. In some embodiments, the initial flowing of cells comprises a high fluid velocity to ensure a uniform, substantially laminar flow (e.g., a plug flow) of cells during inoculation of the one or more substrates within the elongated bioreactor. In one or more embodiments, for example, the elongated bioreactor is filled with cell culture media prior to flowing cells therethrough, and a substantially laminar plug flow is implemented to insert cells therein to prevent mixing of the cells as they push the cell culture media out of the elongated bioreactor.

Upon flowing cells into the elongated bioreactor, flow of material therethrough is arrested or at least partially decelerated for a second period of time in order to allow at least a portion of the cells to settle, land, and/or otherwise adhere to one or more substrates or surfaces disposed within the elongated bioreactor. Then, at an end of the second period of time, cell culture media is circulated through the elongated bioreactor at a progressively increasing flow rate (i.e., gradually accelerating) for a third period of time to provide a gradual rise in shearing forces that allow settled, landed, and/or adhered cells to maintain position on the one or more substrates and resist shear introduced with the rising fluid velocity while promoting growth of the settled, landed, and/or adhered cells. Indeed, by gradually increasing fluid velocity, the disclosed embodiments prevent shearing of settled, landed, and/or adhered cells from substrates at least by avoiding abrupt changes in fluid velocity that could result in increased separation of cells from substrates.

As also mentioned above, the disclosed embodiments enable selective operation of individual bioreactors within a system of bioreactors. For example, in some embodiments, a method for producing a comestible meat product includes growing meat cells within a plurality of elongated bioreactors (e.g., a system of pipe-based bioreactors according to one or more disclosed embodiments) connected in parallel by circulating cell culture media through the elongated bioreactors at one or more cultivation flow rates. Upon growing the meat cells within the plurality of elongate bioreactors, cultured cells are selectively harvested from a first bioreactor by closing valves to other bioreactors of the plurality and flowing fluid through the first bioreactor at an elevated flow rate compared to the one or more cultivation flow rates. Moreover, some embodiments include selectively sanitizing (i.e., cleaning) the first bioreactor by closing valves to other bioreactors of the plurality and flowing sanitation fluid (e.g., steam or cleaning solution) through the first bioreactor. In some embodiments, the sanitation fluid is flowed in an opposite flow direction of the flow direction used during cultivation and harvesting.

As illustrated by the foregoing discussion, the present disclosure utilizes a variety of terms to describe features and advantages of the disclosed methods. Additional detail is now provided regarding the meaning of such terms. For example, as used herein, the term "cells" refers to individual cells of meat. In particular, cells may comprise different cell types, such as one or more of muscle-derived cells, muscle progenitor cells, satellite cells, stem cells, myoblasts, mesangioblasts, myofibroblasts, ectoderm lineage cells, endoderm lineage cells, mesoderm lineage cells, mesenchymal stem cells, hepatocytes, fibroblasts, pericytes, adipocytes, epithelial, chondrocytes, osteoblasts, osteoclasts, pluripotent cells, somatic stem cells, endothelial cells, or other similar cell types. Furthermore, cells may comprise different types of progenitor cells, including myogenic progenitors, adipogenic progenitors, mesenchymal progenitors (e.g., mesenchymal progeny cells), or other types of progenitor cells.

The animal cells can be primary cells and/or cell lines. The methods provided herein are applicable to any metazoan cell in culture. Generally, the animal cells are from any metazoan species whose tissues are suitable for dietary consumption and demonstrate the capacity for skeletal muscle tissue specification. In some embodiments, the animal cells are derived from any non-human animal species intended for human or non-human dietary consumption (e.g., cells of avian, ovine, caprine, porcine, bovine, or piscine origin) (e.g., cells of livestock, poultry, avian, game, or aquatic species).

Additionally, in one or more embodiments, the animal cells are from livestock such as domestic cattle, pigs, sheep, goats, camels, water buffalo, rabbits, and the like. In addition, or in the alternative, in some embodiments, the animal cells are from poultry such as domestic chicken, turkeys, ducks, geese, pigeons, and the like. Further, in one or more embodiments, the animal cells are from game species such as wild deer, gallinaceous fowl, waterfowl, hare, and the like. The animal cells can also be cells from aquatic species or semi-aquatic species harvested commercially from wild fisheries or aquaculture operations, or for sport, including certain fish, crustaceans, mollusks, cephalopods, cetaceans, crocodilians, turtles, frogs, and the like. Additionally, in one or more embodiments, the animal cells are from exotic, conserved or extinct animal species. In some embodiments, the animal cells are from Gallus, Gallus domesticus, Bos taurus, Sous scrofa, Meleagris gallopavo, Anas platyrynchos, Salmo salar, Thunnus thynnus, Ovis aries, Coturnix, Capra aegagrus hircus, or Homarus americanus.

In some embodiments, the animal cells are modifiable by a genetic switch to induce rapid and efficient conversion of the cells to skeletal muscle for cultured production. Additionally, in one or more embodiments, the animal cells are myogenic cells, destined to become muscle, or muscle-like cells. In some embodiments, the myogenic cells are natively myogenic, e.g., myoblasts. Natively myogenic cells include, but are not limited to, mesenchymal progeny, myoblasts, myocytes, satellite cells, side population cells, muscle derived stem cells, mesenchymal stem cells, myogenic pericytes, or mesoangioblasts.

Further, in some embodiments, the animal cells are of the skeletal muscle lineage. Cells of the skeletal muscle lineage include myoblasts, myocytes, and skeletal muscle progenitor cells, also called myogenic progenitors that include satellite cells, side population cells, muscle derived stem cells, mesenchymal stem cells, mesenchymal progeny, myogenic pericytes, and mesoangioblasts. Additionally, in one or more embodiments, the animal cells are non-myogenic, and such non-myogenic cells can be programmed to be myogenic, for example, the cells may comprise fibroblasts modified to express one or more myogenic transcription factors. In exemplary embodiments, the myogenic transcription factors include MYOD1, MYOG, MYF5, MYF6, PAX3, PAX7, paralogs, orthologs, and genetic variants thereof. In some embodiments, the cells are modified to express one or more myogenic transcription factors as described in a PCT publication, WO/2015/066377, incorporated by reference herein in its entirety.

In some embodiments, the animal cells include a mixture of one or more cell populations described herein. For example, the animal cells can include a mixture of fibrogenic cells and myogenic cells in co-culture. In another example, the animal cells can include a mixture of fibroblasts and myoblasts in co-culture. In some embodiments, the animal cells used for the production of comestible cell-based food products for consumption are a mixture of fibroblasts and myoblasts in a suspension co-culture. In some embodiments the animal cells used for the production of comestible cell-based food products for consumption are a mixture of fibroblasts and myoblasts in an adherent co-culture. In some embodiments, the co-culture can further comprise adipocytes.

In some embodiments, the animal cells are genetically modified to inhibit a pathway, e.g., the HIPPO signaling pathway. Exemplary methods to inhibit the HIPPO signaling pathway as described in a PCT Application No. PCT/US2018/031276, incorporated by reference herein in its entirety. Further, in one or more embodiments, the cells are modified to express telomerase reverse transcriptase (TERT) and/or inhibit cyclin-dependent kinase inhibitors (CKI). Additionally, in some embodiments, the cells are modified to express TERT and/or inhibit cyclin-dependent kinase inhibitors as described in a PCT publication, WO 2017/124100, incorporated by reference herein in its entirety.

Additionally, in one or more embodiments, the animal cells are modified to express glutamine synthetase (GS), insulin-like growth factor (IGF), and/or albumin. Exemplary methods of modifying cells to express GS, IGF, and/or albumin are described in a PCT Application No. PCT/US2018/042187 which is incorporated by reference herein in its entirety.

Additionally, it will be appreciated that the animal cells can comprise any combination of the modifications described herein. Similarly, in one or more embodiments, the animal cells can include a combination of the various cell types described herein.

As used herein, the term "suspension cells" (or "suspension") refers to cells growing in an at least partially liquid growth medium in which cells grow, multiply, and/or maintain nourishment. In particular, a suspension includes an agitated growth medium that is housed in a container in which single cells or small aggregates of cells grow, multiply, and/or maintain nourishment from the nutrients of the agitated growth medium. Cells grown in suspension are not attached to a substrate and therefore differ from a conventional adherent culture. As used herein, the term "suspension culture" or "cell suspension culture" refers to a type of culture in which single cells or small aggregates of cells are cultured as non-adherent cells or aggregates of cells.

As used herein, the term "adherent cells" refers to a mass comprising cells of meat. In particular, adherent cells can refer to cellular tissue of cultured meat gathered into a collective mass, including via growth on a substrate. In some embodiments, the cell mass is comestible. Additionally, adherent cells can include cells grown on a substrate that have been nourished by a growth medium to grow during a formation period. Adherent cells may comprise different cell types, such as one or more of muscle-derived cells, muscle progenitor cells, satellite cells, stem cells, myoblasts, mesangioblasts, myofibroblasts, mesenchymal progeny, mesenchymal stem cells, hepatocytes, fibroblasts, pericytes, adipocytes, epithelial, chondrocytes, osteoblasts, osteoclasts, pluripotent cells, somatic stem cells, endothelial cells, or other similar cell types. For example, adherent cells can include a cell sheet of cultured meat growing within an enclosure, such as a chamber, housing, container, etc.

As used herein, the phrases "cell-based meat composition," "cell-based meat," "slaughter-free meat," "slaughter-free cell-based meat," "in vitro produced meat," "in vitro cell-based meat," "cultured meat," "cultivated meat," "slaughter-free cultured meat," "in vitro produced cultured meat," "in vitro meat," "in vitro cultured meat" and other similar such phrases are interchangeably used herein, and refer to the meat that is generated in vitro, starting with cells in culture, and that method which does not involve the slaughter of an animal in order to directly obtain meat from that animal for dietary consumption.

As used herein, the term "substrate" refers to a material on which cells attach or grow. In particular, a substrate includes a material to which cells adhere and upon which cells form a cellular tissue. Accordingly, a substrate can support or promote cell adhesion, cell differentiation, and/or growth of cells to form a cell mass—namely, a comestible meat product. For example, a steel substrate or other substrate can be positioned to receive loaded cell culture media as part of a seeding process inside a bioreactor. Once the cell mass grows to a predetermined size or for a predetermined duration, in some embodiments, the cell mass is harvested from the substrate. The substrate can include a variety of biocompatible materials, such as a metal material, polymer material, organic, or biologic scaffold. The substrate may be porous, have pores of variable size, or otherwise have features that permit at least some components of steam, cleaner, and/or culture media to permeate from one side of a substrate to another side of the substrate. Furthermore, substrate surfaces may be solid, with a variety of surface finishes or textures, including but not limited to electro-polished, electro-plated, sanded, bead-blasted, or etched surface finishes.

As used herein, the term "bioreactor," used interchangeably with the term "cultivator" refers to an apparatus in which cells are seeded, cultivated, and grown to form a cellular tissue of the cell-based meat product. As mentioned above, for instance, one or more substrates for supporting and promoting cell adhesion, cell differentiation, and/or cell growth can be disposed within a cavity or chamber of a bioreactor or cultivator. Bioreactors or cultivators are often part of a closed system for producing cells in a sterile environment. Moreover, the pipe-based bioreactors disclosed herein may optionally be referred to as tissue cultivators, pipe-based cultivators, tissue bioreactors, and so forth.

Figure 1:
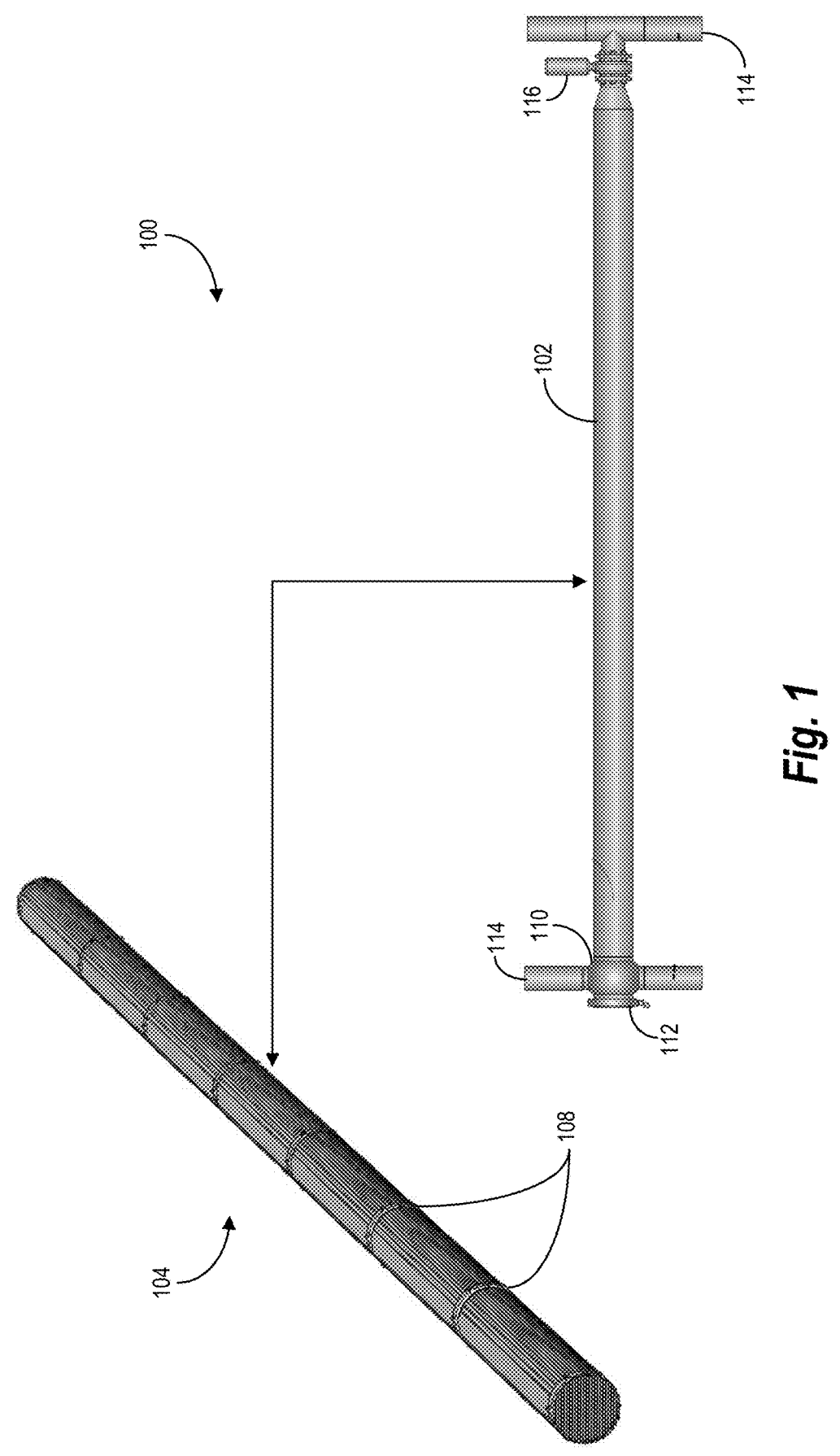
FIG. 1 illustrates a pipe-based bioreactor with a plurality of planar substrates in accordance with one or more embodiments.

Additional detail will now be provided in relation to illustrative figures portraying example embodiments and implementation of the disclosed methods, apparatuses, and systems. For example, FIG. 1 illustrates a pipe-based bioreactor 100 according to one or more embodiments. As illustrated, the pipe-based bioreactor 100 comprises an elongated enclosure 102 (i.e., a pipe) with a plurality of substrates 104 disposed therein. As mentioned previously, the elongated enclosure 102 of the pipe-based bioreactor enables increased fluid velocities and improved flow control (e.g., as discussed in greater detail below in relation to FIG. 13).

As described herein, elongated enclosures can include various shapes and sizes configured to allow for passage of fluid therethrough at relatively high fluid velocities. For example, in some embodiments, the elongated enclosure of a pipe-based bioreactor comprises a cylinder with a relatively small ratio of diameter to length. For example, in one or more embodiments, an elongated bioreactor or pipe-based bioreactor has a diameter-to-length ratio of at least 1:2. More specifically, in one or more embodiments, an elongated bioreactor or pipe-based bioreactor has a diameter-to-length ratio between 1:2 and 1:100, between 1:3 and 1:80, between 1:4 and 1:60, between 1:5 and 1:50, between 1:5 and 1:40, between 1:5 and 1:20, or between 1:5 and 1:10.

For instance, in one or more embodiments, the elongated enclosure comprises a diameter between 4 inches and 16 inches and a length between 4 feet and 40 feet. For instance, in one or more embodiments, the elongated enclosure comprises a pipe with an outer diameter of approximately 4 inches and a length of approximately 8 to 20 feet. In alternative embodiments, the elongated enclosure comprises a pipe with an outer diameter of approximately 8 inches and a length of approximately 10 to 20 feet. In particular, in one or more embodiments the elongated enclosure comprises a pipe with an outer diameter of 4 inches and a length of 10 feet or an outer diameter of 8 inches and a length of 20 feet.

As shown in FIG. 1, the plurality of substrates 104 are arranged to conform to an interior profile of the elongated enclosure 102, as secured by multiple clamps or template rings 108. In some embodiments, the clamps or template rings 108 also secure the substrates 104 at a desired spacing relative to one another to allow for cell growth between substrates. The substrates 104 and/or the clamps/rings 108 can include a variety of bio-compatible materials, such as a metal material, polymer material, organic, or biologic material. In one or more embodiments, the substrates 104 disposed within the elongated enclosure 102 are nominally spaced to provide for growth of meat cells therebetween. For example, in some embodiments, substrates are spaced apart by a distance between 0.5 mm and 10 mm. In some embodiments, the spacing between substrates is between 1 mm and 5 mm. In at least one embodiment, the spacing between substrates is approximately 2.5 mm.

Also, the pipe-based bioreactor 100 may include a hygienic (i.e., aseptic) ball housing 110 with clamp 112 providing access to the plurality of substrates 104 within the elongated enclosure 102. In some embodiments, clamp 112 and/or ball housing 110 also include a transparent piece of material for viewing (i.e., monitoring) the interior of the elongated enclosure 102.

As shown, the elongated enclosure 102 is connected to a fluid source at each end via process connections 114, through which fluid flow direction may be varied as needed. In addition, a valve 116 is secured to the pipe-based bioreactor 100 to provide for adjustment of flow rates within the elongated enclosure 102. In alternative embodiments, additional and/or alternative types of valves, other than those illustrated, are implemented for adjustment of flow rates within the elongated enclosure 102.

Figure 2:
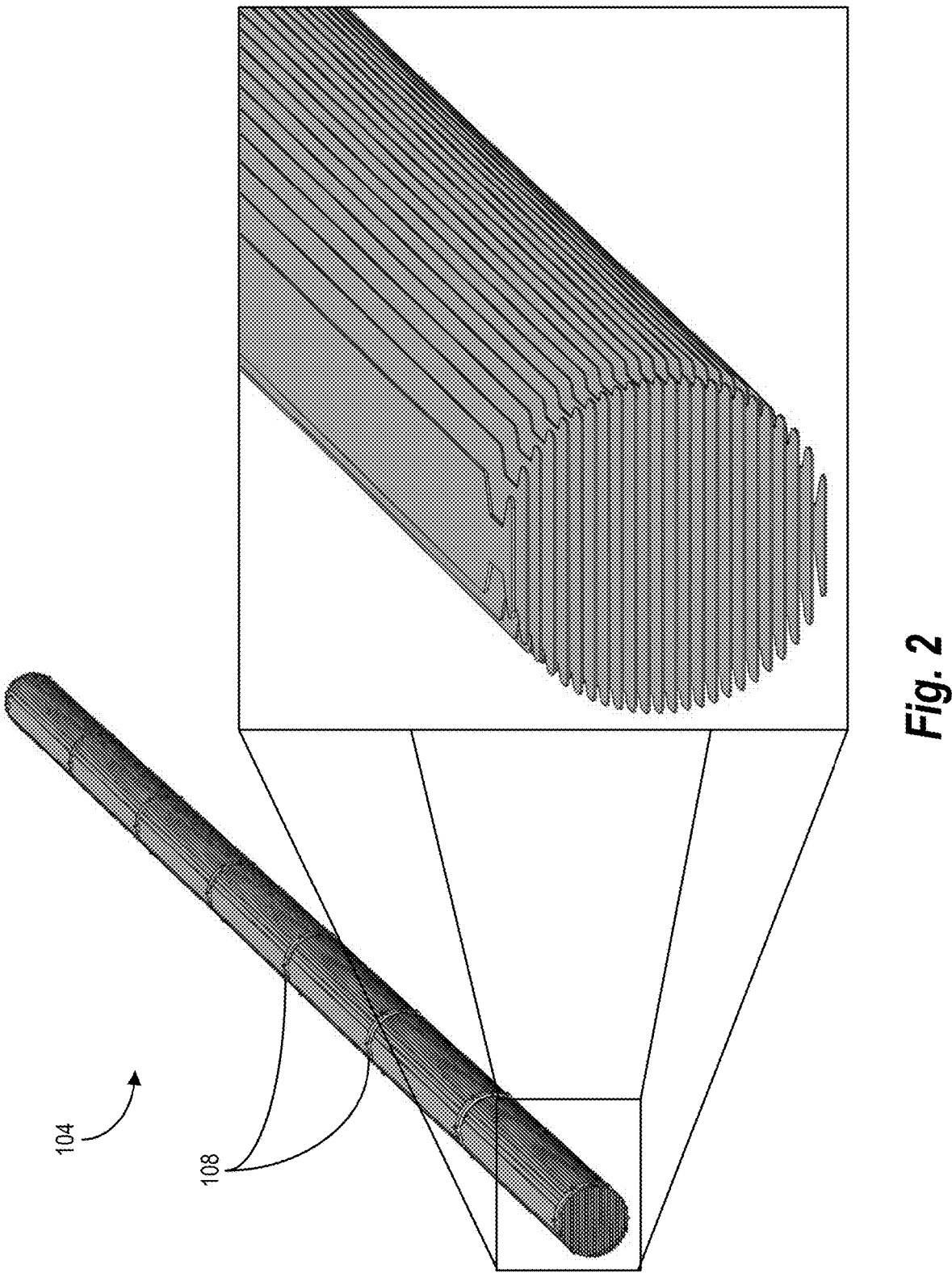
FIG. 2 illustrates a plurality of planar substrates arranged to fit within a pipe-based bioreactor in accordance with one or more embodiments.

Furthermore, FIG. 2 illustrates an expanded view of the plurality of substrates 104 of the pipe-based bioreactor 100 of FIG. 1. In the embodiment shown, the plurality of substrates 104 comprises a series of planar substrates, stacked in parallel and separated from one another to allow for adherence and growth of cells on one or both planar surfaces of each substrate. As shown, the planar substrates of the plurality of substrates 104 comprise various widths to maximize the use of space within the elongated enclosure 102 (see FIG. 1). More specifically, the planar substrates have a relatively small width near the top and bottom of the elongated enclosure 102 and increase in width as they approach the center of the elongated enclosure 102 in a vertical direction along the profile thereof. For instance, in one or more embodiments, the planar substrate proximate to the center of the elongated enclosure 102 has a width approximately the same as the interior diameter thereof, whereas the planar substrates proximate to the top and bottom of the elongated enclosure have widths approximately one third of the interior diameter of the elongated enclosure 102. As also shown, each planar substrate increases in width as they approach the planar substrate proximate the center, such that the plurality of substrates conforms to the interior profile of the elongated enclosure 102.

As shown by FIGS. 1-2, the pipe-based bioreactor 100 can include a plurality of substrates 104 that are stacked vertically. In one or more implementations, the substrates have varying widths. For example, in one or more implementations, at least 50 percent of the substrates have a unique width (e.g., a width that differs from the widths of the other substrates). In alternative implementations, each of the substrates has a unique width. In still further embodiments, pairs of substrates have the same width that is unique from other pairs of substrates. In such implementations, a pair of substrates comprise substrates that are equally spaced from the center of the pipe-based bioreactor 100.

In one or more embodiments, the center substrate(s) have a width greater than the other substrates. For example, the center substrate can comprise a single substrate positioned at the center of the pipe-based bioreactor 100. Alternatively, the center substrates can comprise a pair of substrates that are nearest to the center of the pipe-based bioreactor 100 and are equally distant from the center (e.g., longitudinal axis) of the pipe-based bioreactor 100. In other words, the center substrate(s) have the largest width. The substrates have widths that decrease as the substrates move away from the center of the pipe-based bioreactor 100. In this manner, the substrate(s) farthest from the center of the pipe-based bioreactor 100 have the smallest width. In one or more implementations, each substrate on a first side of the center substrate(s) has a unique width. Similarly, each substrate on an opposing side (e.g., a second side) of the center substrate(s) has a unique width. In such implementations, the plurality of substrates 104 comprises pairs of substrates with the same width (e.g., a substrate on one side of the center of the pipe-based bioreactor 100 and a corresponding substrate on an opposing side of the center of the pipe-based bioreactor 100).

In one or more implementations, the pipe-based bioreactor 100 comprises between 6 and 50 substrates. More particularly, in one or more implementations the pipe-based bioreactor 100 comprises between 10 and 40 substrates or between 20 and 30 substrates. For example, FIG. 2 illustrates an implementation of a pipe-based bioreactor 100 with 24 plates. One will appreciate in light of the disclosure herein that the total number of substrates is dictated by the diameter of the pipe-based bioreactor 100 and the spacing between adjacent substrates. The exemplary embodiment of FIG. 2, the pipe-based bioreactor 100 comprises an even number of substrates. In alternative implementation, the pipe-based bioreactor 100 comprises an odd number of substrates.

In the embodiment shown in FIG. 2, the pipe-based bioreactor 100 comprises substrates with 12 unique widths. More particularly, the pipe-based bioreactor 100 comprises 12 pairs of substates, where each pair of substrates comprises a different width than each other pair of substrates. In one or more alternative implementations, the pipe-based bioreactor 100 comprises substrates with at least 3 unique widths. In alternative implementations, the pipe-based bioreactor 100 comprises substrates with at least 5, 10, 15, 20, or 25 unique widths. In one or more implementations, the pipe-based bioreactor 100 comprises substrates with between 3 and 20 unique widths.

As shown by FIG. 2, in one or more implementations, the pipe-based bioreactor 100 comprises a plurality of stacked substrates with offset edges. For example, in one or more embodiments, each substrate of the pipe-based bioreactor 100 terminates at a different point than immediately adjacent substrate(s). In other words, each substrate of the pipe-based bioreactor 100 comprises a width that differs than each immediately adjacent substrate(s).

FIGS. 1-2 also illustrate that in one or more embodiments the pipe-based bioreactor 100 comprises a plurality of planar substrates housed within a curved or circular elongated enclosure 102. Furthermore, in one or more implementations, each planar substrate extends along an entire length of the elongated enclosure 102. In alternative implementations, each planar substrate extends between 90 and 100 percent of the length of the elongated enclosure 102. In still further implementations, each planar substrate extends between 95 and 100 percent of the length of the elongated enclosure 102.

Moreover, while the plurality of substrates 104 of FIGS. 1-2 comprise one configuration of horizontally arranged planar substrates, embodiments of the present disclosure include various configurations of nominally spaced substrates conforming to the interior of an elongated enclosure, such as but not limited to vertically arranged planar substrates, a honeycomb lattice, one or more spiral substrates, a plurality of concentric circular substrates, a packed tube, an empty tube, packed rods, or corrugated sheets.

Figure 3:
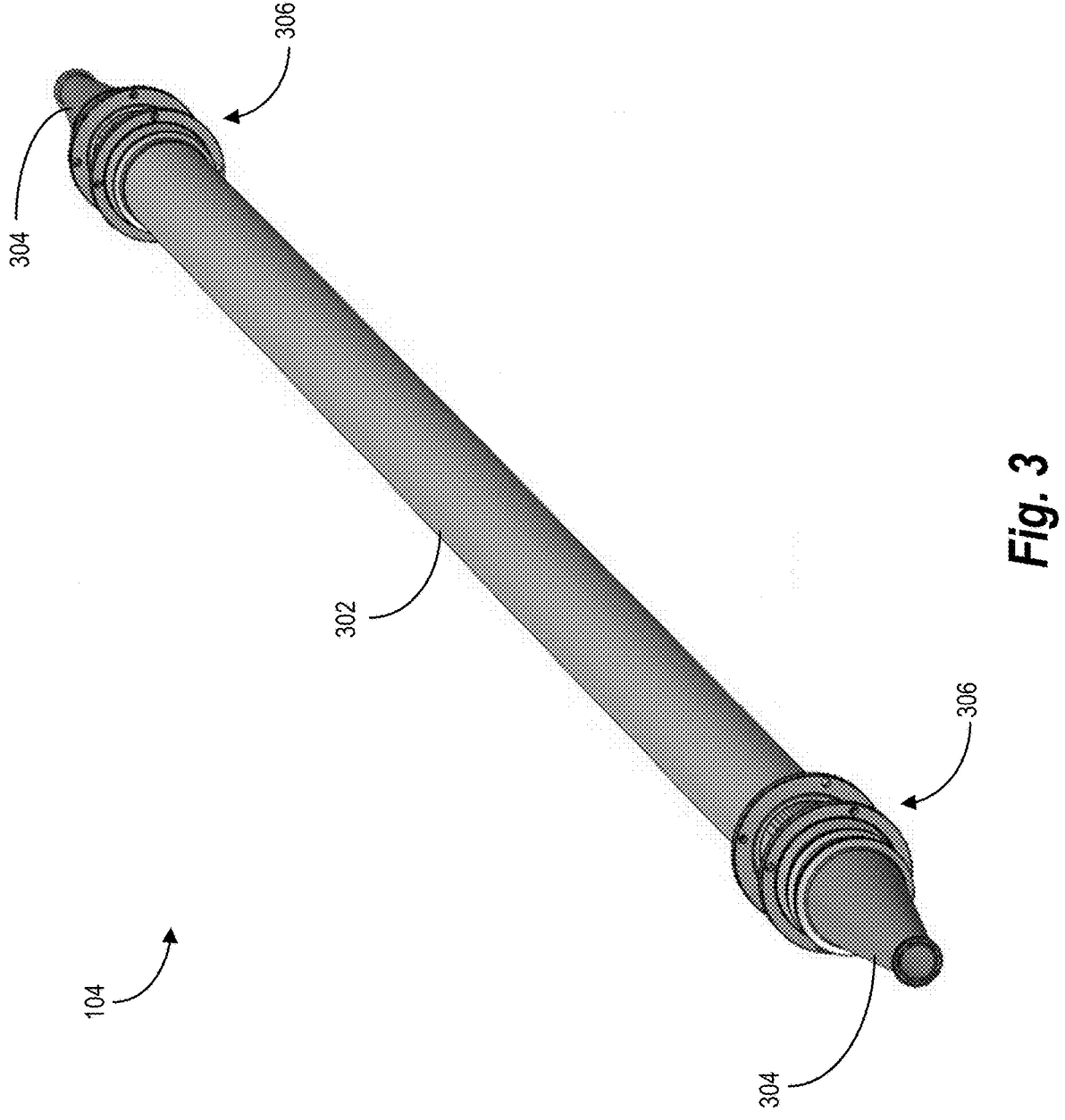
FIG. 3 illustrates a pipe-based bioreactor in accordance with one or more embodiments.

FIG. 3 illustrates an embodiment of a pipe-based bioreactor 300 implementing additional features useful in the preparation of cell-based meat products. For instance, sight glasses 306 are secured to each end of elongated enclosure 302 to enable monitoring of cell adherence, cell growth, cell harvesting, and cleaning of the pipe-based bioreactor 300. The sight glasses can comprise a clear material (glass, borosilicate glass, polycarbonate, etc.) that allows for viewing of the interior of the pipe-based bioreactor 300. As shown in FIG. 3, some embodiments include sight glasses 306 that encircle the entire circumference of the elongated enclosure 302. Alternative embodiments include sight glasses that only cover a portion of the circumference of the elongated enclosure, such as but not limited to a square, rectangular, or circular sight glass. Also, some embodiments include additional sight glasses to enable monitoring of the interior of the pipe-based bioreactor at various locations. For example, in one or more embodiments, the sight glass extends along an entire length of the elongated enclosure 302 of the pipe-based bioreactor 300.

In some embodiments, additional or alternative means are provided for monitoring the contents of the pipe-based bioreactor. For example, a variety of sensor can be implemented to measure and/or monitor temperature, PH-levels, internal pressure, and so forth. Furthermore, the pipe-based bioreactor design ensures that measurements taken at one position within the bioreactor are relatively consistent with other positions within the bioreactor, compared to conventional systems having significantly larger internal volumes. Accordingly, in one or more implementations, single measurements can be taken within a pipe-based bioreactor that represent the whole interior of the bioreactor with an increased level of accuracy.

Moreover, the pipe-based bioreactor 300 includes plumbing reducers 304 at each end of the elongated enclosure 302. As mentioned previously, the disclosed embodiments of pipe-based bioreactors enable increased fluid velocities and improved flow control by virtue of the pipe-based design. Various configurations of plumbing can be used to regulate fluid flow with embodiments of the pipe-based bioreactor, such as but not limited to the illustrated plumbing reducers 304. For example, in one or more embodiments, offset or eccentric plumbing at opposing ends of the pipe-based bioreactor (i.e., inlets and outlets) to prevent (or reduce) pooling of fluid at either end thereof, such as described below in relation to FIG. 8 and as shown in FIGS. 8, 14-17, and 20.

Additionally, in some embodiments, offset or eccentric plumbing enables the pipe-based bioreactor to be fully drained of fluid during each process of meat product production. For example, such plumbing allows condensate to leave the pipe-based bioreactor during steaming in place (and cleaning in place) and allows gas bubbles to escape upward and out of the pipe-based bioreactor, thus preventing dead zones (areas with limited cell growth) within the pipe-based bioreactor.

Figure 4:
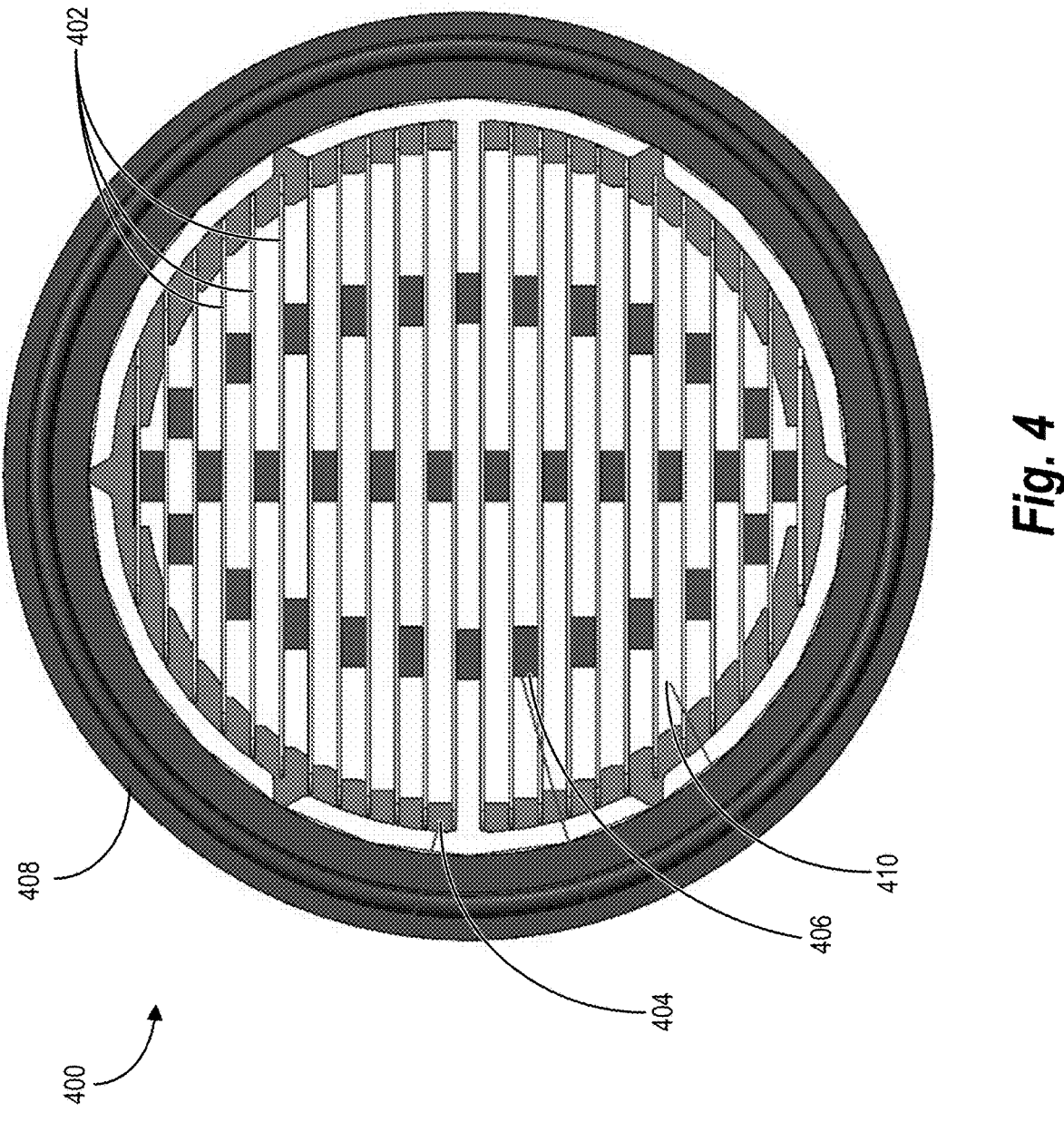
FIG. 4 illustrates a plurality of planar substrates conforming to an interior profile of a pipe-based bioreactor in accordance with one or more embodiments.

FIG. 4 illustrates a cross sectional view of an embodiment of a pipe-based bioreactor 400 implementing a plurality of planar substrates 402 conforming to an interior profile of an elongated enclosure (enclosure not pictured due to the viewing angle). As shown by FIG. 4, the pipe-based bioreactor 400 can comprise a circular cross section. In alternative implementations, the pipe-based bioreactor 400 comprises an elliptical, triangular, square, rectangular, rectangular with rounded edges, hexagonal, octagonal, or other shaped cross section.

The pipe-based bioreactor is securable to a system via a tri-clamp gasket 408, or other means operable to secure pipes together in a closed system. As shown, the plurality of planar substrates 402 are secured in place by one or more retaining rings 404 comprised of Teflon or another suitable material, such as but not limited to silicone, rubber, or plastic. In alternative embodiments, the retaining rings 404 are not included.

In addition, the plurality of planar substrates 402 are spaced apart by strips 406 comprised of silicone or another suitable material, such as but not limited to Teflon, rubber, or plastic. In alternative embodiments the plurality of planar substrates 402 are spaced apart by indentations, grooves, ridges, or protrusions in the substrates themselves, such as but not limited to the configuration discussed below in relation to FIG. 5A. The spacing between layers of the plurality of planar substrates 402 is thus maintained to create space for adhered cells to grow on each substrate during the cultivation process. In some embodiments, for example, the planar substrates 402 are spaced apart from one another by a gap between 0.005 and 0.025 inches. For instance, in one or more embodiments the planar substrates 402 are spaced apart by a spacing distance of between 0.01 and 1.0 inches, between 0.05 and 0.5 inches, between 0.07 inches and 0.15 inches. In particular, in one or more embodiments the spacing distance comprises 0.100 inches or 0.125 inches.

As mentioned above, embodiments of the pipe-based bioreactor include various configurations of substrates conforming to the inside of an elongated enclosure. For example, FIGS. 5A through 5E illustrate cross sectional views of pipe-based bioreactors 500a through 500e, respectively, implementing various exemplary alternative configurations of substrates. Various alternative embodiments include configurations of substrates not shown herein, such as but not limited to a packed tube, an empty tube, packed rods, or corrugated sheets.

Figure 5A:
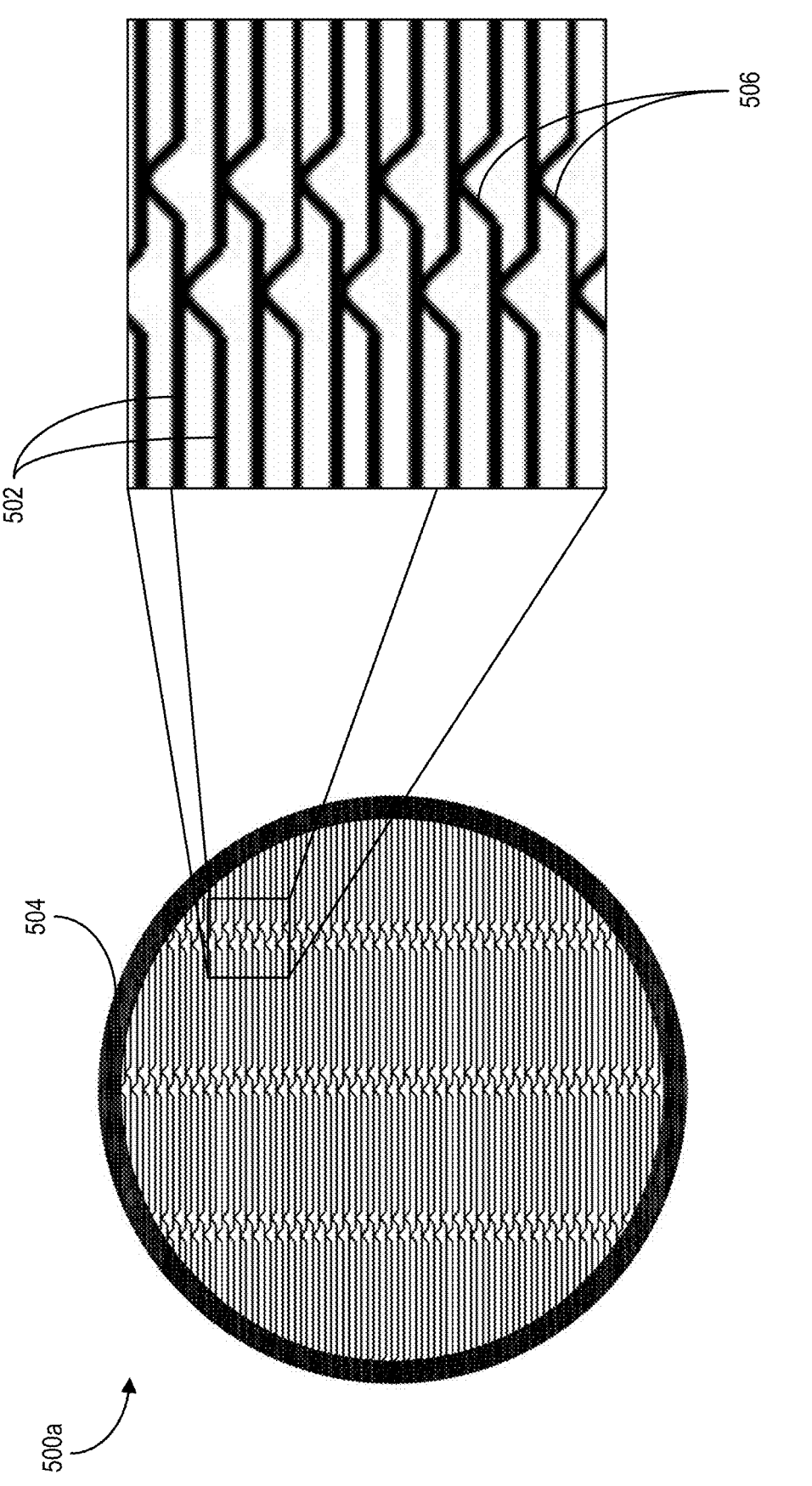
FIGS. 5A-5E illustrate various arrangements of substrates within a pipe-based bioreactor in accordance with one or more embodiments.

As shown in FIG. 5A, the pipe-based bioreactor 500a includes a plurality of substantially planar substrates 502 in a stacked configuration within an enclosure 504. As illustrated, each substrate of the plurality of substrates 502 is separated by indents or ridges 506 in the substrates themselves, thus eliminating the necessity of spacers, adhesive strips, and/or retaining rings for maintaining the spacing between substrates. Such substrates that include indents or ridges are considered substantially planar substrates. In one or more embodiments, for example, each indent or ridge 506 comprises a bend (i.e., a protrusion) of the substrate plate protruding to contact each neighboring plate, thus forming a gap (e.g., a spacing distance) between adjacent substrates. As shown, each of the plurality of substrates 502 includes three bends/protrusions to secure the distance between substrate plates and reduce bending of the substrate plates under load. Alternative embodiments include more or fewer bends/protrusions than shown in FIG. 5A.

Figure 5B:
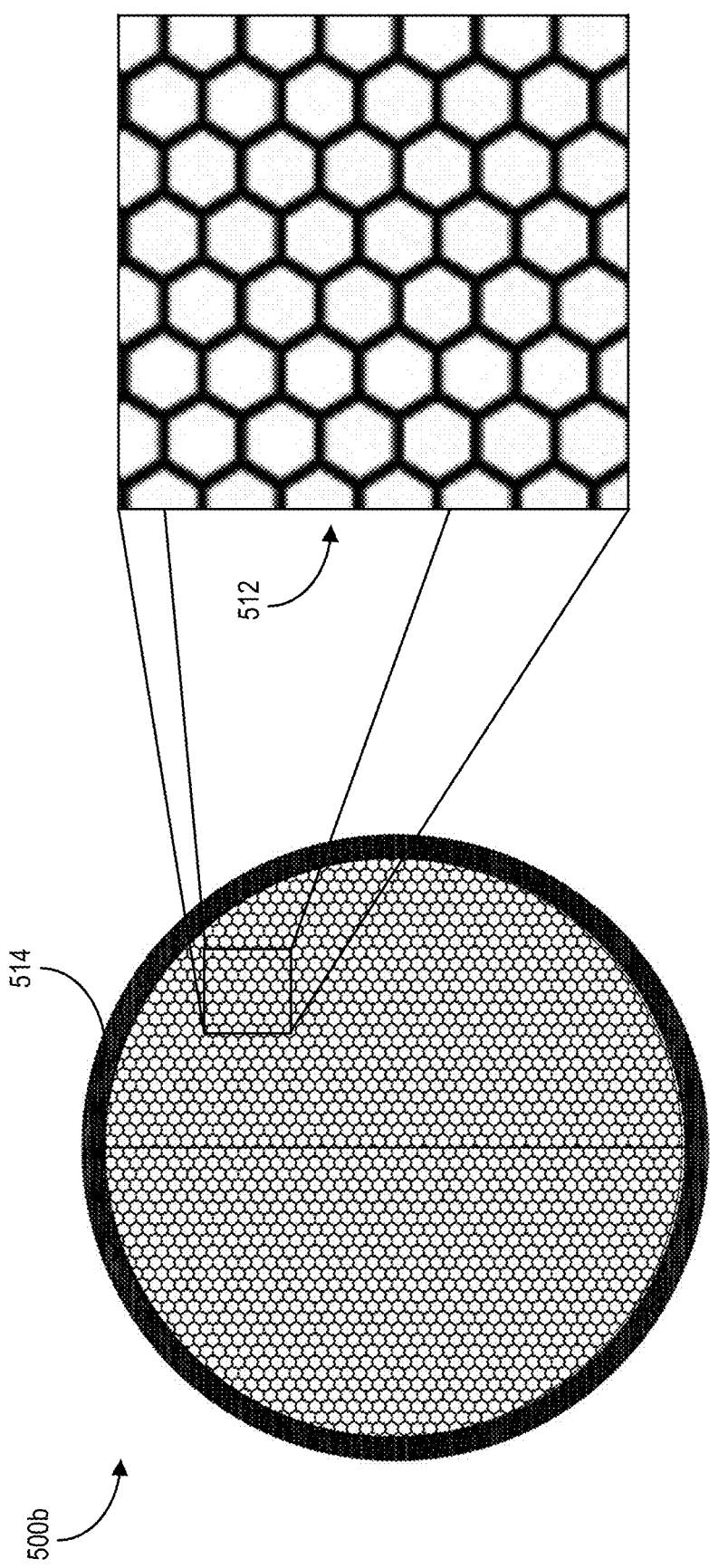

As shown in FIG. 5B, the pipe-based bioreactor 500*b* includes a honeycomb lattice 512 of substrate material conforming to the interior of an elongated enclosure 514. For example, each pod of the honeycomb lattice 512 comprises a hexagon cross section extending into the elongated enclosure 514 of pipe-based bioreactor 500*b* (i.e., into the page as illustrated), with sufficient pods to fill the interior profile thereof. In alternative embodiments, the honeycomb lattice comprises pods of various profiles, such as but not limited to a circle, square, pentagon, and so forth.

As illustrated, each pod of the honeycomb lattice 512 provides an area to which cells can adhere and grow while allowing for fluid to pass therethrough. Indeed, various of different configurations of substrates conforming to the interior of a pipe-based bioreactor can be implemented to produce cell-based meat products according to the present disclosure.

Figures 5C, 5D:
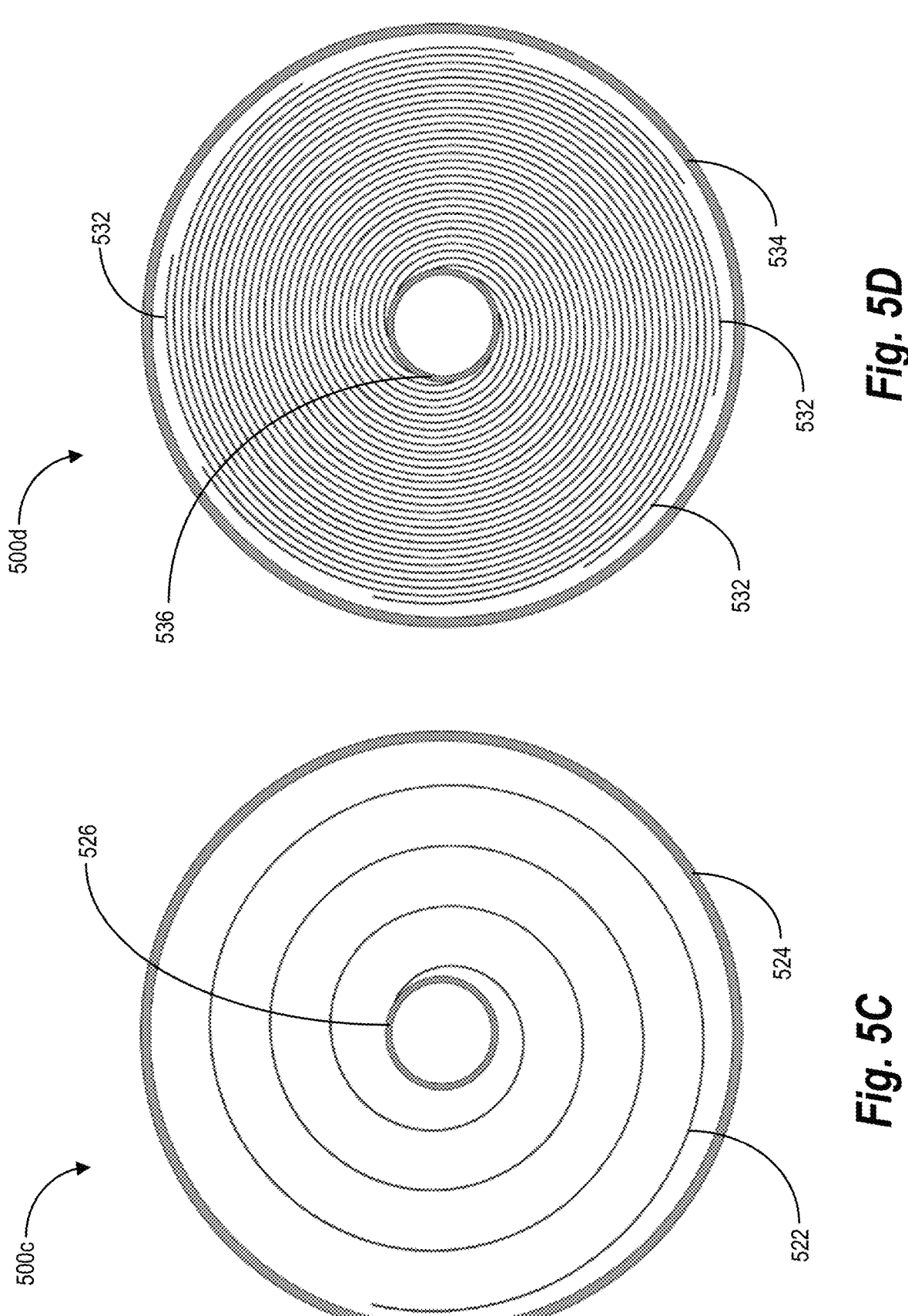

As shown in FIG. 5C, the pipe-based bioreactor 500*c* includes a spiral substrate 522 conforming to the interior of an elongated enclosure 524. As illustrated, the spiral substrate 522 originates at and is secured to a cylinder 526 proximate a central axis of the elongated enclosure 524. Alternatively, in one or more embodiments, the spiral substrate 522 is secured to and/or originates at an interior surface of the elongated enclosure 524. Also, while not shown in FIG. 5C, the spiral substrate 522 can be secured within the pipe-based bioreactor 500*c* by alternative or additional structures, such as but not limited to a mesh, a lattice, or individual elements between adjacent surfaces of the spiral substrate 522.

As shown in FIG. 5D the pipe-based bioreactor 500*d* includes multiple leafed spiral substrates 532 conforming to the interior of an elongated enclosure 534. As illustrated, each spiral substrate 532 originates at and is secured to a cylinder 536 proximate a central axis of the elongated enclosure 534. Alternatively, in one or more embodiments, one or more of the spiral substrates 532 is secured to and/or originates at an interior surface of the elongated enclosure 534. Also, while not shown in FIG. 5D, each of the spiral substrates 532 can be secured within the pipe-based bioreactor 500*d* by alternative or additional structures, such as but not limited to a mesh, a lattice, or individual elements between adjacent surfaces of the spiral substrates 532.

Moreover, while the pipe-based bioreactors 500*c* and 500*d* are shown having respective cylinders 526 and 536 proximate a central axis thereof, embodiments can omit such an element or include alternative elements, such as but not limited to a solid bar or wire or a protruded square or other profile shape.

Figure 5E:
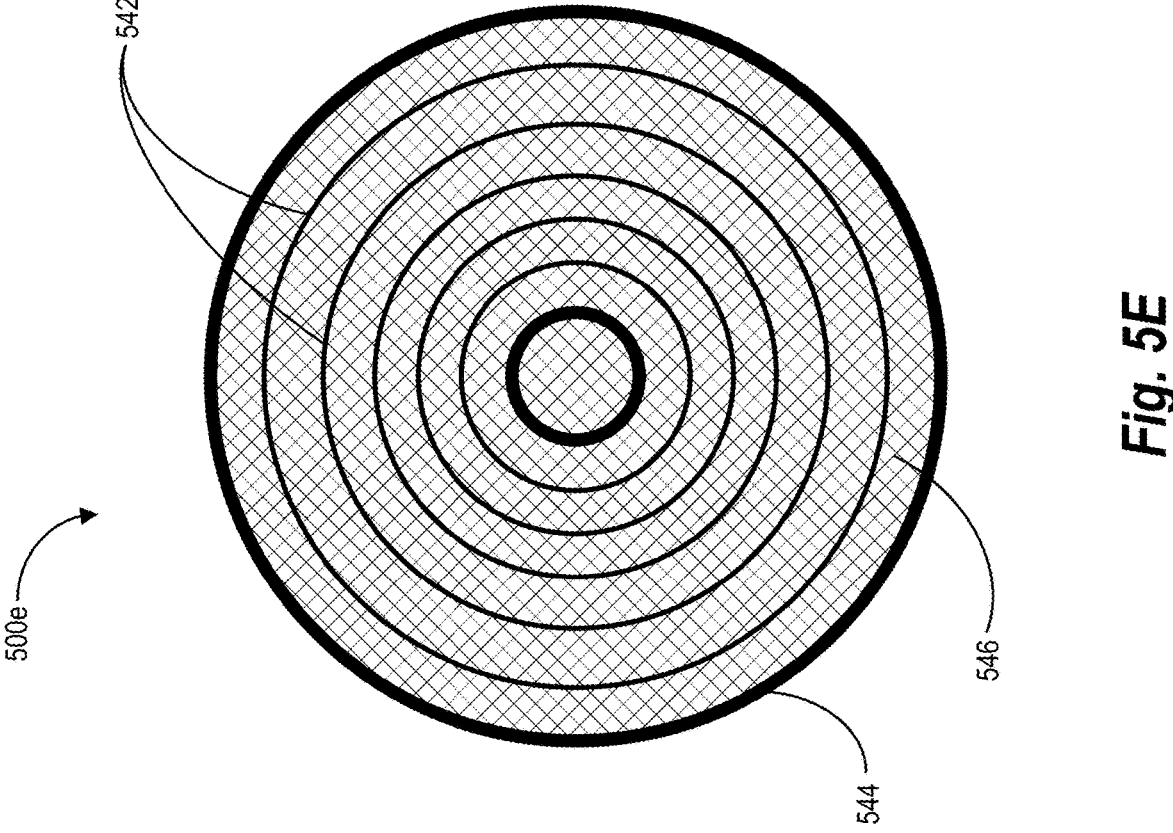

As shown in FIG. 5E, the pipe-based bioreactor 500*e* includes a plurality of substrates comprising nominally spaced concentric rings 542 that conform to the interior of an elongated enclosure 544. As illustrated the concentric rings 542 are secured within the elongated enclosure 544 by a mesh interlock 546 that maintains gaps between adjacent concentric rings 542. Alternatively, or additionally, the concentric rings 542 can be secured utilizing individual elements between adjacent concentric rings 542. In one or more implementations, each the pipe-based bioreactor 100 comprise two mesh interlocks 546 (one at an end of the pipe-based bioreactor 100 and one at an opposing end of the pipe-based bioreactor 100). Alternatively, the pipe-based bioreactor 100 comprises more than two mesh interlocks 546. For example, the pipe-based bioreactor 100 comprises three mesh interlocks 546 (one at each end of the pipe-based bioreactor 100 and one at the middle of the pipe-based bioreactor 100). In still further implementations, the pipe-based bioreactor 100 comprises a plurality of equally spaced mesh interlocks 546.

Figure 6:
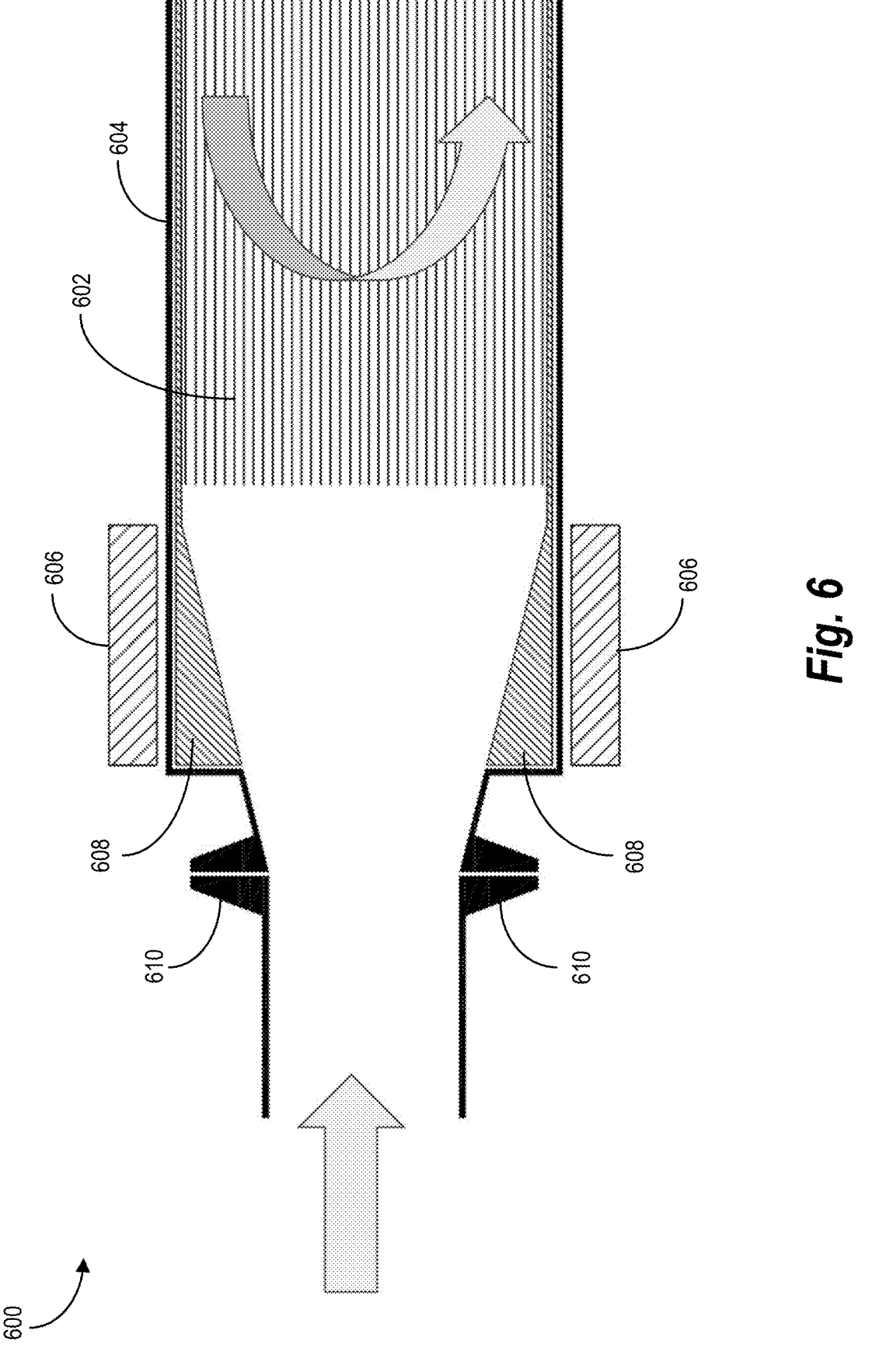
FIG. 6 illustrates a pipe-based bioreactor with magnetically rotatable substrates in accordance with one or more embodiments.

As mentioned previously, in some embodiments, pipe-based bioreactors and/or the substrates disposed therein are rotatable to allow for cells to be seeded to opposing sides of the substrates. For example, FIG. 6 illustrates a cross sectional view of a pipe-based bioreactor 600 implementing rotatable substrates 602 within an elongated enclosure 604. As shown, the substrates 602 are secured to a ferrous or magnetic coupling 608 within the elongated enclosure 604, the coupling 608 itself being rotatable within the enclosure 604. An external electromagnet 606 is implemented to rotate the ferrous or magnetic coupling 608 within the elongated enclosure 604, thus also rotating the substrates 602 without opening the enclosure 604.

In alternative embodiments, substrates disposed within a pipe-based bioreactor are rotatable without the use of a magnetic apparatus. For example, in one or more embodiments, substrates are secured to a rotatable coupling within an elongated enclosure of a pipe-based bioreactor, the rotatable coupling having one or more handles or flanges protruding outside of the enclosure to allow for a machine or operator to rotate the rotatable coupling from without. Alternatively, a remote motor can be implemented within the closed system of the pipe-based bioreactor to enable rotation of the rotatable coupling while maintaining a closed, sterile system within the elongated enclosure.

Accordingly, with the pipe-based bioreactor 600 secured to a fluid source via a tri-clamp 610 (or other available connection hardware), cells can be injected into the elongated enclosure 604 with the substrates 602 in a first planar position to allow for the cells to adhere to a top side of the substrates 602. Then, utilizing the external electromagnet 606, the substrates 602 are rotated 180 degrees before seeding the opposite sides thereof with cells. Thus, the substrates 602 can be seeded on both sides to effectively double the amount of cell production in the pipe-based bioreactor 600. In addition, the substrates 602 can be rotated during or prior to other cultivation, harvesting, or cleaning processes when repositioning of the substrates 602 is advantageous.

Figure 7:
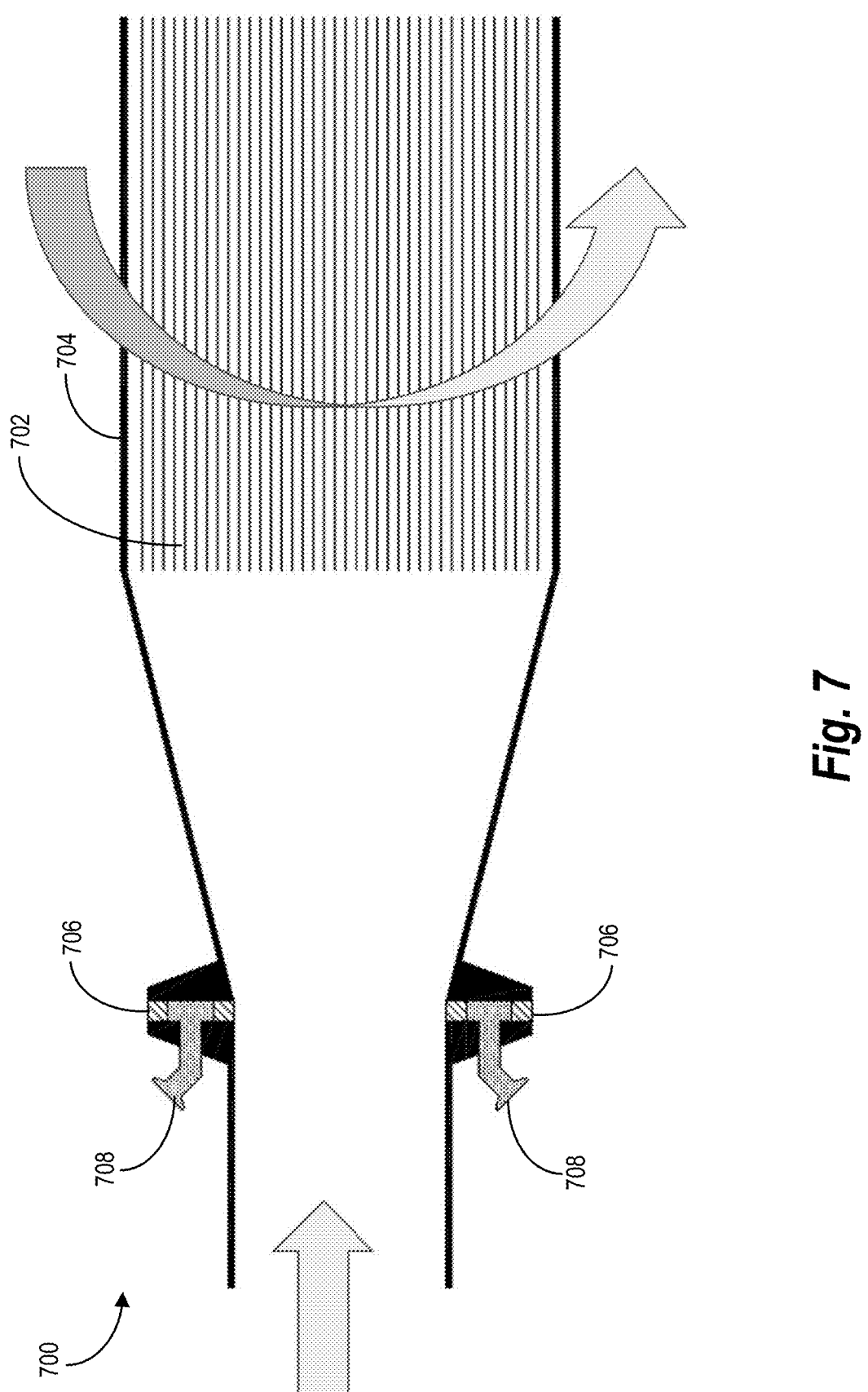
FIG. 7 illustrates a mechanically sealed rotatable pipe-based bioreactor in accordance with one or more embodiments.

Alternatively, in some embodiments, the elongated enclosure of the pipe-based bioreactor can be rotated (as opposed to rotating the interior substrates with the enclosure fixed) to allow for seeding of planar substrates on both sides. For example, FIG. 7 illustrates a pipe-based bioreactor 700 secured to a fluid source via a rotary fluid coupling 706 (i.e., a mechanical coupling) having fluid connections 708. The pipe-based bioreactor 700 comprises multiple planar substrates 702 fixedly secured within an elongated enclosure 704, such that rotation of the planar substrates requires rotation of the elongated enclosure 704.

As an alternative to rotation, or as a further supplementation to disperse seeding, porous substrates and/or agitated flow may be used to further facilitate seeding on opposing sides of a substrate. In some embodiments, the substrates are oriented vertically within the pipe-based bioreactor to allow seeding on both sides, the substrates remaining vertical or returning to horizontal during growth, harvest, and cleaning. Alternatively or additionally, cells flowed into a pipe-based bioreactor for seeding can be configured to float rather than settle (i.e., reduced in density relative to an ambient fluid), such that the floating cells can rise and adhere to an underside of a substrate.

As shown, the pipe-based bioreactor 700 is rotatable by virtue of the rotary fluid coupling 706 having fluid inlets

708. In other embodiments, alternative rotatable couplings can be used, such as coupling having ball bearings or other means of controlled rotation. Accordingly, cells can be injected from a connected fluid source into the elongated enclosure 704 with the enclosure positioned such that the substrates 702 are in a first planar position to allow for the cells to adhere to a top side of the substrates 702. Then, utilizing the rotary fluid coupling 706 (or other rotatable coupling) to rotate the elongated enclosure 704, the substrates 702 are rotated 180 degrees before seeding the opposite sides thereof with cells. Thus, the substrates 702 can be seeded on both sides to effectively double the amount of cell production in the pipe-based bioreactor 700. In addition, the elongated enclosure 704 can be rotated during or prior to other cultivation, harvesting, or cleaning processes when repositioning of the substrates 702 is advantageous.

In some embodiments, a pipe-based bioreactor and/or the one or more substrates disposed therein are continuously rotatable. For instance, in some implementations, the pipe-based bioreactor can be rotated continuously at a relatively slow rate to allow cells to settle and adhere on surfaces of the one or more substrates within the pipe-based bioreactor. For example, in embodiments comprising non-planar substrates (e.g., spiral or circular substrates such as illustrated in FIGS. 5C-5E), the pipe-based bioreactor can be rotated continuously to allow cells to settle and adhere to curved surfaces within the pipe-based bioreactor.

Figure 8:
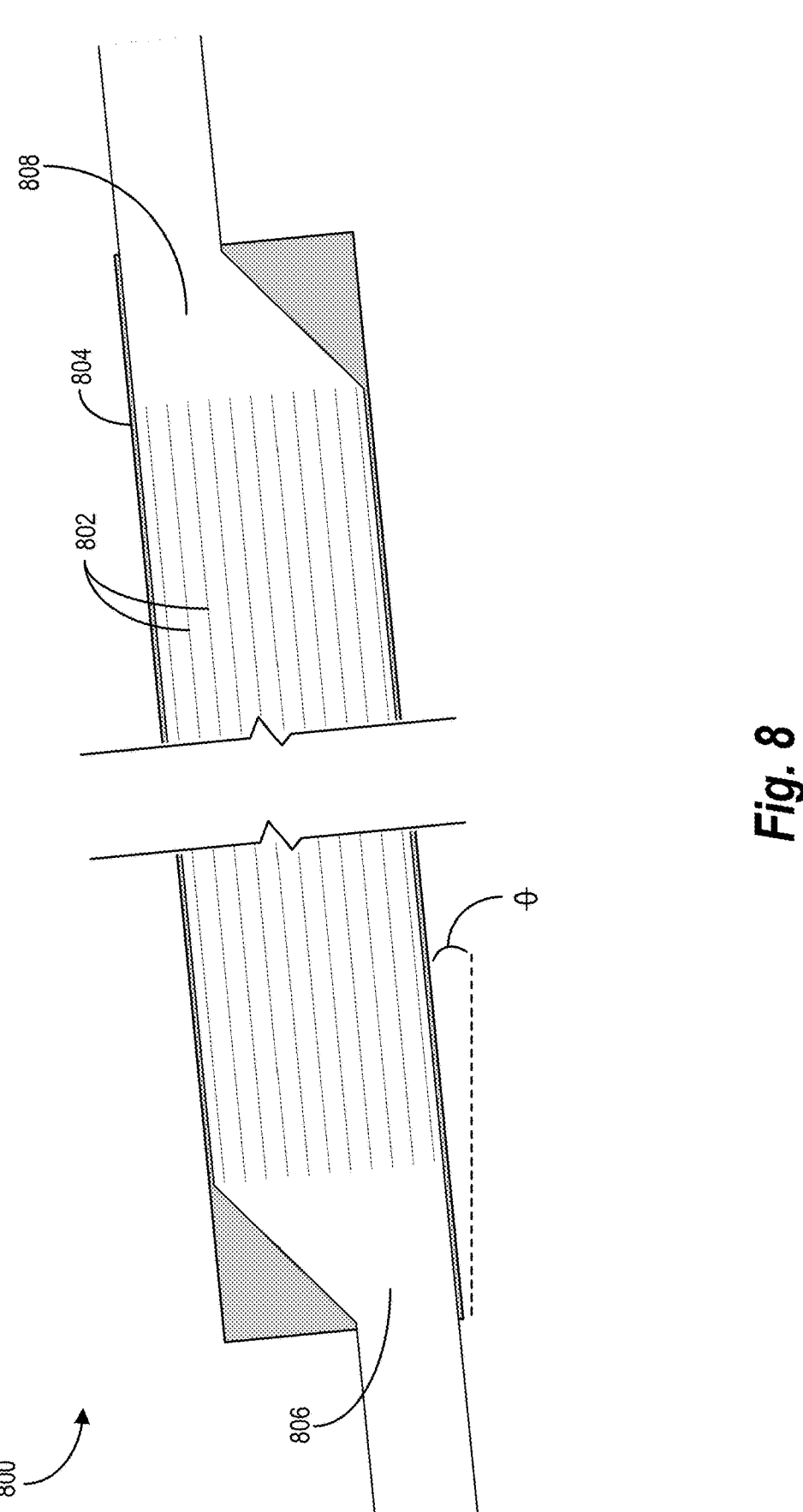
FIG. 8 illustrates a pipe-based bioreactor with an offset inlet and an offset outlet in accordance with one or more embodiments.

Furthermore, in some embodiments, the pipe-based bioreactor is mounted at an incline relative to the ground to take advantage of gravitational forces during certain processes in the preparation of cell-based meat products. For example, FIG. 8 illustrates a pipe-based bioreactor 800 with multiple planar substrates 802 disposed within an elongated enclosure 804 mounted at an angle θ relative to the ground. In one or more embodiments, the angle θ is between 1 degree and 89 degrees. In other words, the angle θ is not parallel or perpendicular to a horizontal plane. In some embodiments, for example, the angle θ is between 1 and 45 degrees, between 5 and 25 degrees, or between 5 and 15 degrees. For instance, in one or more embodiments, the angle θ of the pipe-based bioreactor 800 is approximately 10 degrees relative to a horizontal plane. In some implementations, a ground surface supporting the pipe-based bioreactor represents the horizontal plane.

Indeed, with the pipe-based bioreactor 800 at an incline, accumulation of steam condensation (i.e., pooling) is reduced during steaming for sanitation in a flow direction from right to left, when referencing FIG. 8, and accumulation of gas bubbles during cultivation is reduced in a flow direction from left to right, when referencing FIG. 8. As further illustrated, the pipe-based bioreactor 800 comprises offset inlets/outlets 808. As shown, the offset inlets/outlets 808 prevent collection (i.e., pooling) of fluid or gas bubbles at the respective entry and exit of the elongated enclosure 804.

In one or more embodiments, a pipe-based bioreactor and/or the substrates disposed therein are rotated continuously during cell growth. Continuous rotation advantageously provides regular, repeating variations in gravitational forces experienced by adhered cells during growth and differentiation. In some implementations, during continuous rotation, the flow of fluid may be adjusted such that the interior of the pipe-based bioreactor is only partially filled with liquid. In other words, continuous rotation may be paired with a flow rate of cell culture media that only partially fills the pipe-based reactor at any given time, wherein the adhered cells cycle between a submerged, liquid environment and an exposed, gaseous environment (e.g., air). In some examples, the pipe-based reactor is filled between about 10 and 90 percent, between about 20 and 80 percent, between about 30 and 70 percent, between about 40 and 60 percent, or at about 50 percent. In some embodiments, the angle of incline of a pipe-based bioreactor is selectively adjustable, such that the pipe-based bioreactor can be tilted at various angles relative to a ground surface during various procedures. In some instances, an angle of the pipe-based reactor is set relatively horizontal to a ground surface to provide a relatively consistent submerge cycle across a length of the pipe-based reactor. For example, a relatively horizontal angle ensures that the partially filled bioreactor has sufficient liquid on a higher end thereof. In one example, the relatively horizontal angle from a ground surface is between about 1 and 5 degrees, between about 1 and 4 degrees, between about 1 and 3 degrees, or between about 1 and 2 degrees. With the pipe-based bioreactor partially filled, continuously rotated, and minimally angled, the cells therein may beneficially experience variations in fluid exposure and gravitational forces in a regular repeating pattern, thus providing regular and tolerable stress to the cells to promote robust tissue formation during cultivation of cells. Additionally, providing variable conditions for adherent cells in terms of regular submerge cycles and regular oscillations in gravity facilitate robust cell growth that is better able to differentiate into tissue with strong connections to neighboring cells and is more resistant to oxidative stress.

Figure 9:
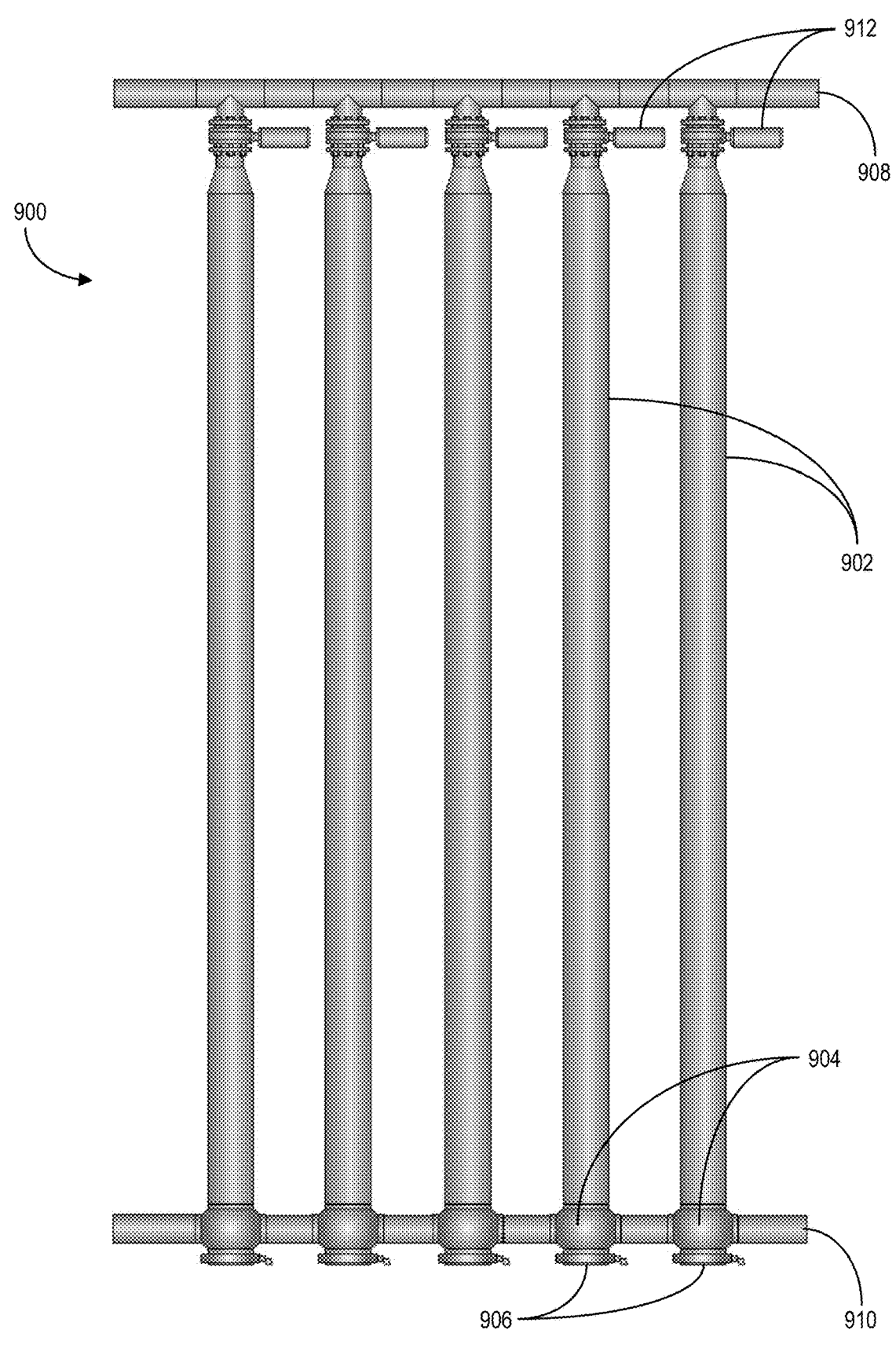
FIG. 9 illustrates a series of interconnected pipe-based bioreactors in accordance with one or more embodiments.

In some embodiments, a plurality of pipe-based bioreactors is interconnected, such as but not limited to in series or in parallel, to a fluid source to enable increased production of cell-based meat products. For example, FIG. 9 illustrates a bioreactor system 900 of pipe-based bioreactors 902 connected in parallel to a fluid source via process connections 908, 910. While the bioreactor system 900 is shown having five pipe-based bioreactors in parallel, other embodiments can include additional or fewer pipe-based bioreactors and can include pipe-based bioreactors in parallel, side-by-side, in series (i.e., connected axially for increased overall length), or any combination thereof. As shown, each pipe-based bioreactor 902 is optionally secured to process connection 910 with a hygienic (aseptic) ball housing 906. Alternative hardware for connection of the pipe-based bioreactors to a fluid source and to one another are also anticipated within the scope of this disclosure.

With the pipe-based bioreactors 902 arranged in an interconnected system, the bioreactor system 900 is upscaled with relatively low cost and effort compared to other methods for expansion. For example, to increase the size of a single pipe-based bioreactor (i.e., by increasing the length and/or diameter of the elongated enclosure) can result in increased cost of materials, as well as a necessity for larger pumps in order to achieve similar flow rates and flow distributions within the enlarged enclosures. In contrast, interconnecting the pipe-based bioreactors 902 enables nearly unlimited upscaling/expansion of the bioreactor system 900 without detrimental effects to operable flow rates and/or flow distributions within each pipe-based bioreactor 902. For instance, in some embodiments, a single build specification for a pipe-based bioreactor is used to construct a system of virtually any number of pipe-based bioreactors without the need to design or implement additional customized parts.

As also shown in FIG. 9, a pneumatic butterfly valve 912 is secured at a second end of each pipe-based bioreactor 902 for flow control and/or shutoff. While not shown in FIG. 9, some embodiments include additional valves for selective opening and shutting of each pipe-based reactor 902 in the system 900. Indeed, another advantage of the foregoing configuration of pipe-based bioreactors 902 connected in parallel is the ability to close off one or more of the pipe-based bioreactors 902 from the fluid source while flowing fluid through one or more opened pipe-based bioreactors 902. Thus, one or more pipe-based bioreactors 902 can be operated at a time, allowing for further increased flow rates and flow control by temporarily limiting the size of the open system.

As shown by FIG. 9, in one or more implementations, a system for growing meat cells to form a comestible cell-based meat product comprises a plurality of elongated bioreactors 902 where each bioreactor has a diameter of less than 20 inches. In alternative implementations, a system for growing meat cells to form a comestible cell-based meat product comprises a plurality of elongated bioreactors 902 where each bioreactor has a diameter of less than 25, 15, 12, 10, or 8 inches.

In one or more implementations, a system for growing meat cells to form a comestible cell-based meat product comprises a plurality of elongated bioreactors 902 where each bioreactor has a diameter-to-length ratio of at least 1:2. More specifically, in one or more embodiments, a system for growing meat cells to form a comestible cell-based meat product comprises a plurality of elongated bioreactors 902 where each bioreactor has a diameter-to-length ratio between 1:2 and 1:100, between 1:3 and 1:80, between 1:4 and 1:60, between 1:5 and 1:50, between 1:5 and 1:40, between 1:5 and 1:20, or between 1:5 and 1:10.

Additionally, or alternatively, a system for growing meat cells to form a comestible cell-based meat product comprises a plurality of elongated bioreactors 902 each comprising a plurality of planar substrates configured to grow cells where each substrate, or pair of substrates, has a unique width.

As mentioned previously, some embodiments include a plurality of pipe-based bioreactors connected in series to enable increased production of cell-based meat products. For example, FIG. 10 illustrates a bioreactor system 1000 implementing multiple pipe-based bioreactors 1002 connected in pairs for increased length. As further illustrated, five pairs of pipe-based bioreactors 1002 connected in series are in turn connected in parallel to a fluid source via process connections 1012, 1014. Also, each inline pair of pipe-based bioreactors 1002 are secured by a ball housing 1016 having a viewing glass 1018 for observation and inspection of the interior of each inline bioreactor. An additional ball housing 1008 secures each inline pair of pipe-based bioreactors 1002 to the process connection 1014 at a first end, and a valve 1010 is secured proximate the process connection 1012 at a second end for flow control and/or shutoff of each inline pair of pipe-based bioreactors 1002.

Moreover, as mentioned previously, pipe-based bioreactors can be rotated to enable seeding of meat cells on both sides of each substrate disposed therein. For example, bioreactor system 1000 of FIG. 10 is secured to a mounting rack 1004 such that the bioreactor system 1000 can be rotated about axis 1006. Furthermore, while FIG. 10 illustrates the bioreactor system 1000 rotatably mounted for rotation about axis 1006 (i.e., rotation about a horizontal axis), alternative embodiments are mounted such that rotation of either the entire system or each individual pipe-based bioreactor is operable about a vertical axis, such as described above in relation to FIG. 7.

As mentioned previously, in some embodiments, a plurality of pipe-based bioreactors is connected in parallel to a fluid source for preparing cell-based meat products. For example, FIG. 11 illustrates a bioreactor system 1100 comprising a plurality of pipe-based bioreactors 1102 connected in parallel to a fluid source 1106 (e.g., a media tank for housing cell culture media). As shown, a plurality of valves 1104 is secured to the plurality of pipe-based bioreactors 1102 to enable individual use of each pipe-based bioreactor 1102. For instance, to limit flow to only a first bioreactor of the plurality of pipe-based bioreactors 1102, the valve 1104 of the first bioreactor is opened while the remaining valves 1104 are closed.

Also, the bioreactor system 1100 includes a pump 1110 for pumping fluid through the bioreactor system 1100. For example, in some embodiments, meat cells are cultivated in each pipe-based bioreactor 1102 by flowing a cell culture media 1108 therethrough in a first flow direction (i.e., counterclockwise in FIG. 11). Indeed, in some embodiments, each pipe-based bioreactor 1102 is seeded, cultivated, and harvested in the first flow direction. Moreover, each pipe-based bioreactor 1102 can be sanitized, for example, by flowing steam in a second flow direction (i.e., clockwise in FIG. 11). Further still, in some embodiments, the fluid source 1106 can be cleaned separately from the plurality of pipe-based bioreactors 1102 by closing all the valves 1104 prior to cleaning and/or steaming the fluid source 1106. In one or more implementations, each of the elongated bioreactors is of the plurality of pipe-based bioreactors 1102 is mounted at an incline relative to a ground surface to reduce accumulation of condensation within the elongated bioreactor when flowing steam through the elongated bioreactors.

Furthermore, while many of the illustrated embodiments show particular direction of flow for each process or procedure, such flow directions can be reversed. During cultivation, for example, the flow direction of cell culture media can be changed intermittently to ensure a more uniform oxygen gradient within the pipe-based bioreactor (i.e., by intermittently reversing the oxygen gradient across the pipe-based bioreactor), thus enabling use of longer pipe-based bioreactors. In addition, harvesting can be done in either or both directions to achieve greater separation of adhered cells. Similarly, cleaning in both directions may be implemented to remove materials more effectively from within a pipe-based bioreactor prior to steaming.

To further illustrate, FIG. 12 illustrates an example process for preparing comestible cell-based meat products in accordance with one or more embodiments. More specifically, in one or more embodiments, meat cells (i.e., adherent cells) are prepared by performing an act 1202 of arranging one or more cell culture substrates. In one or more embodiments, the cell culture substrates comprise a permeable substrate (e.g., permeable to physiological solutions) or an impermeable substrate (e.g., impermeable to physiological solutions). The substrate for the adherent cells can be flat, concave, or convex. Additionally, the substrate for the adherent cells can be textured so as to promote cell growth. In particular, act 1202 can involve placing a plurality of elongated substrates within an elongated enclosure of a pipe-based reactor.

Further, as shown in FIG. 12, the adherent cells can be prepared by performing an act 1204 of contacting cells to a surface of the substrate. To illustrate, in one or more embodiments, the adherent cells are prepared by contacting cell culture substrates to a cultivation infrastructure, including within a pipe-based bioreactor according to one or more embodiments disclosed herein. More detail regarding act 1204 is provided below in relation to FIG. 13 and FIG. 15.

In some embodiments, the culturing of adherent cells can induce the production of extracellular matrix (ECM). Indeed, in one or more embodiments, the ECM can act as an autologous scaffold to direct three-dimensional cellular growth. For example, in some embodiments, the ECM can direct attachment, proliferation, and hypertrophy of cells on a plane perpendicular to the substrate. In addition, or in the alternative, in some embodiments, the cultivation infrastructure may not comprise an exogenously added scaffold to promote self-assembly of a three-dimensional cellular biomass. In some embodiments, the cultivation infrastructure may not comprise exogenous scaffolds such as a hydrogel or soft agar.

As mentioned above, adherent cells can be grown to form a cell sheet. Accordingly, an exemplary method of producing cell-based meat comprises: (a) providing fibroblasts and/or myoblasts from a non-human organism; (b) culturing the fibroblasts and/or myoblasts in media under conditions under which the fibroblasts and/or myoblasts grow in either suspension culture or adherent culture, wherein the media is substantially free of serum and other components derived from an animal.

Additionally, as shown in FIG. 12, in one or more embodiments, the adherent cells are prepared by performing an act 1206 of growing cells on the substrate(s). In one or more embodiments, the adherent cells are grown on a suitable substrate that is specifically treated to allow cell adhesion and spreading, such as a surface located within a sterile, pipe-based bioreactor. The culturing conditions for the generation of the animal cells for a comestible cell-based food product are generally aseptic and sterile. For example, cells are injected into a cultivation tank, such as an adherent bioreactor, such as a pipe-based bioreactor. The cultivator (i.e., bioreactor) contains the substrate(s) (e.g., metal planks, sheets, or a lattice) to which cells can adhere. The cells are flowed through the enclosure of the pipe-based bioreactor to allow cells to adhere to the substrate over time as described in greater detail in relation to FIG. 13 and FIG. 16.

Before seeding the cells onto the substrate, in some embodiments, the disclosed methods include preparing the substrate, such as by adding or flowing over adherent media to increase cell adherence to the substrate. As suggested above, in some implementations, the substrate is located within a bioreactor enclosure that is a sterile environment. To prepare the substrate in a bioreactor, the disclosed methods can include adding adherent media. The adherent media can be low in calcium to limit cellular clumping, so the cells spread out evenly across the substrate. The adherent media further facilitates attachment by the cells to the substrate. In some implementations, preparing the substrate further includes adding conditioning media and bringing the conditioning media up to temperature. The conditioning media further prepares the substrate by controlling pH, carbon dioxide, and oxygen levels within the cultivation tank. Additionally, the conditioning media may coat the substrates such that the adherence capability of the later seeded cells is enhanced.

The disclosed methods include growing the cells into a cellular tissue. Generally, the seeded cells (including the seeded initial cells and the previously unlanded cells) are grown in conditions that allow the formation of cellular tissue for a formation period. In some cases, the formation period can equal 4-14 days. During the formation period, cells may be provided with additional nutrients, media, growth factors, and other supplements to promote cellular growth. For example, the disclosed methods can include providing growth media on day 1. The growth media can include growth factors and beneficial proteins. At nutrient intervals (e.g., every three days) during the formation period, additional feeds, amino acids, proteins, vitamins, minerals, and growth factors may be added to the cultivation tank to support growth in the seeded cells. Additionally, or alternatively, the disclosed methods include adding pre-harvest media before harvest. For instance, three days before harvest, a pre-harvest media including yeast concentrate may be added to the cultivation tank.

In one or more embodiments, the adherent cells include cellular tissue of cultured meat gathered into a collective or agglomerated mass, including via growth on a substrate. In one or more embodiments, the cultivation infrastructure for cultivating the adherent cells has a three-dimensional structure or shape for cultivating a monolayer of adherent cells. Additionally, in some embodiments, the cultivation infrastructure can promote the adherent cells to form a three-dimensional growth of metazoan cells in the cultivation infrastructure to provide a scaffold-less self-assembly of a three-dimensional cellular biomass.

In some embodiments, the adherent cells are grown on a three-dimensional cultivation infrastructure. The three-dimensional cultivation infrastructure may be sculpted into different sizes, shapes, and forms, as desired, to provide the shape and form for the adherent cells to grow and resemble different types of muscle tissues such as steak, tenderloin, shank, chicken breast, drumstick, lamb chops, fish filet, lobster tail, etc. The three-dimensional cultivation infrastructure may be made from natural or synthetic biomaterials that are non-toxic so that they may not be harmful if ingested. Natural biomaterials may include, for example, collagen, fibronectin, laminin, or other extracellular matrices. Synthetic biomaterials may include, for example, hydroxyapatite, alginate, polyglycolic acid, polylactic acid, or their copolymers. The three-dimensional cultivation infrastructure may be formed as a solid or semisolid support.

A cultivation infrastructure can be of any scale and support any volume of cellular biomass and culturing reagents. In some embodiments, the cultivation infrastructure ranges from about 10 µL to about 100,000 L. In exemplary embodiments, the cultivation infrastructure is about 10 µL, about 100 µL, about 1 mL, about 10 mL, about 100 mL, about 1 L, about 10 L, about 100 L, about 1000 L, about 10,000 L, or even about 100,000 L.

In one or more embodiments, the comestible cell-based food product, unless otherwise manipulated to include, does not include vascular tissues, such as veins and arteries, whereas conventional meat does contain such vasculature, and contains the blood found in the vasculature. Accordingly, in some embodiments, the comestible cell-based food product does not comprise any vasculature.

Likewise, comestible cell-based food product, although composed of muscle or muscle-like tissues, unless otherwise manipulated to include, does not comprise functioning muscle tissue. Accordingly, in some embodiments, the cell-based meat does not comprise functioning muscle tissue. It is noted that features such as vasculature and functional muscle tissue can be further engineered into the cell-based meat, should there be a desire to do so.

Also, as shown in FIG. 12, the adherent cells can be prepared by performing an act 1208 of detaching a cell sheet from the substrate. In one or more embodiments, the adherent cells are harvested by detaching a cell sheet from the substrate. In particular, the adherent cells are harvested based on various factors. The adherent tissue may be harvested after a proliferation time period. For example, the adherent cells are harvested after the cells have been growing for anywhere between 4 and 14 days. In another example, the adherent cells are harvested based on completing a proliferation phase. More specifically, the adherent cells may be harvested when the cell sheet starts contracting and stops growing. For instance, the cell sheet may begin to detach from the substrate. In one or more embodiments, the cell sheet is detached from the substrate after adding preharvest media before harvest.

As shown by FIG. 12, the method can optionally involve reducing the moisture and/or size of an agglomeration (e.g., the cell sheet) of adherent cells. For example, act 1210 can involve reducing a moisture content in the adherent cells by vacuum drying the adherent cells. In addition, in some embodiments, act 1210 involves reducing a size of the meat cells via chopping, or other technique. Furthermore, act 1210 can involve forming the cells into the shape of a meat product (e.g., chicken breast, steak).

To further illustrate, FIG. 13 includes a graph depiction 1300 of the various flow rates utilized in the preparation of cell-based meat products within pipe-based bioreactors, according to one or more embodiments. As illustrated, the y-axis represents fluid velocity (i.e., flow rate) within a pipe-based bioreactor and the x-axis represents the approximate time in the meat cell preparation process.

Starting with a sterilized pipe-based bioreactor (e.g., by steaming or similar cleaning methods), meat cells are loaded at an inoculation plug flow rate 1302 until the pipe-based bioreactor is completely filled with cell culture media. In some embodiments, for example, cells are loaded at an inoculation plug flow rate 1302 corresponding to a fluid velocity of 5 to 10 mm/s for 10 minutes. The plug flow 1302 operates at a relatively high flow rate to increase fluid displacement while reducing fluid mixing compared to lower flow rates. Accordingly, the primary objective of the plug flow 1302 is to fully displace the cell culture media with inoculation material (i.e., adherent cells) until the pipe-based bioreactor is overfilled to ensure cell contact with the entire surface area of each substrate disposed therein (e.g., by 10-20%).

With the pipe-based bioreactor filled with cell culture media, valves to the pipe are closed to induce zero-velocity seeding flow 1304 to allow cells within the cell culture media to settle and adhere to the substrates within the pipe-based bioreactor. In some embodiments, for example, the zero-velocity seeding flow 1304 is maintained for 30 minutes to 4 hours to permit cells to adhere to the adherence substrates of the pipe-based bioreactor. Alternatively, in some embodiments, the zero-velocity seeding flow 1304 is replaced with a relatively low (but non-zero) flow for a similar time period.

Once the cells of the cell culture media have been allowed to settle and adhere to the substrates, valves to the pipe-based bioreactor are opened and cell culture media is again flowed across the substrates at a gradually increasing cultivation flow rate 1308. The cultivation flow rate 1308 starts at a relatively low initial flow rate 1306 to prevent shearing forces that would separate (i.e., rip) adhered cells from the substrates. As shown, the cultivation flow rate 1308 is gradually increased from the initial flow rate 1306 until reaching a maximum flow rate 1310. In some embodiments, for example, the cultivation flow 1308 is gradually increased from an initial flow rate 1306 corresponding to a fluid velocity of 0.5 mm/s to a maximum flow rate 1310 corresponding to a fluid velocity of 5 mm/s. As an alternative to the gradual increase in flow rate shown, the cultivation flow rate 1308 can be increased in a stepwise manner to progressively increase the cultivation flow rate 1308 from the initial flow rate 1306 to the maximum flow rate 1310. In some embodiments, the cultivation flow rate 1308 operates within the range between initial flow rate 1306 and maximum flow rate 1310 for a period of 7 to 11 days to allow the adhered cells time to cultivate and grow.

After cultivation, the adhered and cultivated cells are harvested at an elevated harvest flow rate 1312. The harvest flow rate 1312 is elevated to induce a sharp increase in shear force between the adhered and cultivated cells, thus removing the cells for harvest. In some embodiments, for example, fluid flow is increased to a harvest flow rate 1312 corresponding to a fluid velocity of 1000 mm/s for a period of 10 to 30 minutes. In some embodiments wherein a bioreactor system comprises a plurality of interconnected pipe-based bioreactors coupled to the fluid source, the harvest flow rate 1312 is applied to a single pipe-based bioreactor at a time (or batches of two or more pipe-based bioreactors) whilst cells are collected for preparation of cell-based meat products (e.g., as described below in relation to FIGS. 18 and 19).

After harvesting the cells from the pipe-based bioreactor (or system of pipe-based bioreactors), the pipe-based bioreactor(s) are cleaned at a cleaning flow rate 1314 in preparation for another round of inoculation, cultivation, and harvest. In some embodiments, for example, the cleaning flow rate 1314 has a fluid velocity of 1500 mm/s and operates for 30 to 90 minutes. In some embodiments, pulsation, ramping, and deramping of flow is additionally or alternatively implemented to further induce sharp increases in shear to remove materials from within the pipe-based bioreactor during cleaning and/or harvesting. In one or more embodiments, the cleaning fluid comprises a caustic acid that, in some instances, is heated. In some embodiments, each pipe-based bioreactor is individually cleaned while valves to the remaining pipe-based bioreactors are closed. Alternatively, some embodiments include cleaning the system of pipe-based bioreactors simultaneously. Moreover, in cases where harvesting is accomplished without opening the system and/or the pipe-based bioreactor, the cleaning step may be skipped as the sterility of the system is maintained.

Relatedly, FIGS. 14-20 illustrate a plurality of pipe-based bioreactors connected in parallel and configured to operate according to the processes discussed above in relation to FIG. 13. For instance, FIG. 14 illustrates a bioreactor system 1400 implementing a steam in place (SIP) procedure, according to one or more embodiments, for cleaning pipe-based bioreactors 1402 within the system 1400. As shown, the bioreactor system 1400 includes four interconnected pipe-based bioreactors 1402 connected in parallel to a fluid source 1408 containing a cell culture media 1410, as well as a fluid pump 1406 for flowing the cell culture media 1410 and other fluids into the pipe-based bioreactors 1402. When steaming one or more of the pipe-based bioreactors 1402, in some embodiments, steam from a steam source 1412 is flowed in a clockwise direction, with reference to the perspective of FIG. 14 as indicated by arrows, through pipe-based reactors 1402 and into a steam trap 1414.

Moreover, as shown in FIG. 14, one or more of the pipe-based reactors 1402 can be steamed in place without steaming or otherwise disturbing the fluid source 1408 by shutting source valves 1416a and 1416b and opening bioreactor system valves 1418a and 1418b and steam valves 1420a and 1420b. Also, the fluid source 1408 can be steamed in place separately, without steaming or otherwise disturbing the pipe-based bioreactors 1402, by closing bioreactor system valves 1418a and 1418b and opening source valves 1416*a* and 1416*b* and steam valves 1420*a* and 1420*b*. Also, each pipe-based bioreactor 1402 can be steamed in place separately (i.e., one at a time) by use of corresponding inlet valves 1404.

Furthermore, as shown in FIG. 14, each of the pipe-based bioreactors 1402 is inclined relative to horizontal (i.e., relative to the ground). With the pipe-based bioreactors 1402 mounted at an incline, condensation during steaming in place is pulled by gravity towards the steam trap 1414, thus preventing accumulation of condensation within the pipe-based bioreactors 1402. In addition, in some embodiments, each of the pipe-based bioreactors 1402 includes offset outlets 1422 and inlets 1424 to further prevent accumulation of fluid at opposing ends thereof. Accordingly, after traversing each pipe-based bioreactor 1402, the steam exits the system 1400 through an open steam valve 1420*a* into the steam trap 1414.

FIG. 15 illustrates a bioreactor system 1500 implementing an inoculation procedure, according to one or more embodiments, for seeding (i.e., adhering cells to internal substrates) pipe-based bioreactors 1502 within the system 1500. As shown, the bioreactor system 1500 includes four pipe-based bioreactors 1502 connected in parallel to a fluid source 1508 containing a cell culture media 1510. Prior to inoculation (i.e., seeding), one or more of the pipe-based bioreactors 1502 are filled with cell culture media 1510 from fluid source 1508. During inoculation, an inoculation valve 1514 is opened and inoculation cells 1512 are flowed into a given pipe-based bioreactor 1502 at a plug flow rate in a counter-clockwise direction (e.g., using a pump 1506). In some embodiments, the plug flow rate is configured to displace loaded cell culture media within the given pipe-based bioreactor 1502 and replace it with an inoculation bolus (i.e., a prescribed dose of inoculation cells 1512) while reducing mixing of inoculation cells 1512 with the cell culture media 1510 within the given pipe-based bioreactor 1502. For example, in some embodiments, the plug flow rate has a fluid velocity of 10 mm/s.

In some embodiments, the inoculation bolus is larger than the given pipe-based bioreactor 1502 in order to overfill the give pipe-based bioreactor 1502 to ensure maximum adherence of inoculation cells 1510 to the substrates disposed within the given pipe-based bioreactor 1502. For example, in some embodiments, the inoculation bolus is larger than the given pipe-based bioreactor by between 10% and 20%. After the given pipe-based bioreactor is loaded with the inoculation bolus, the corresponding inlet valve 1504 is closed and the inoculation cells are allowed to settle and adhere to substrates disposed within the given pipe-based bioreactor 1402. For example, in some embodiments, an inoculated pipe-based bioreactor is allowed to rest (i.e., with zero flow of fluid or very low flow) for between 30 minutes and 4 hours. In one or more embodiments, the pipe-based bioreactors are thus inoculated separately (i.e., one at a time) by use of corresponding inlet valves 1504.

FIG. 16 illustrates a bioreactor system 1600 implementing a cultivation procedure, according to one or more embodiments, for cultivating cells (i.e., promoting cell growth) within pipe-based bioreactors 1602 of the system 1600. As shown, the bioreactor system 1600 includes four pipe-based bioreactors 1602 connected in parallel to a fluid source 1608 containing a cell culture media 1610. With the pipe-based bioreactors 1602 inoculated (i.e., seeded) as discussed above in relation to FIG. 15, cell culture media 1610 is flowed at a gradually increasing cultivation flow rate in a counter-clockwise direction (e.g., using a pump 1606). In some embodiments, for example, the cultivation flow rate starts at a fluid velocity of 0.5 mm/s and is gradually raised to a fluid velocity between 5 and 6 mm/s. As previously mentioned, the cultivation flow rate is maintained at an upper end of the velocity range for a cultivation period. For example, in some embodiments, the cultivation period is between 7 and 11 days.

As mentioned previously, the cultivation flow rate starts at a relatively low fluid velocity to reduce shearing of adhered cells from substrates within the pipe-based bioreactors 1602. Moreover, the cultivation flow rate is gradually increased to reduce separation of adherent cells while increasing oxygen delivered by cell culture media 1610 to the cells within the pipe-based bioreactors 1602.

Furthermore, as shown in FIG. 16, each of the pipe-based bioreactors 1602 is inclined relative to horizontal (i.e., relative to the ground). With the pipe-based bioreactors 1602 mounted at an incline, buoyant gas bubbles (e.g., oxygen bubbles) float upward towards the fluid source 1608, thus preventing accumulation of gases within the pipe-based bioreactors 1602 during cultivation and other processes. In addition, in some embodiments, each of the pipe-based bioreactors 1602 includes offset outlets 1624 and inlets 1622 to further prevent accumulation of gases at opposing ends thereof.

FIG. 17 illustrates a bioreactor system 1700 implementing a harvest in place (HIP) procedure, according to one or more embodiments, for harvesting cultured cells from within pipe-based bioreactors 1702 of the system 1700. As shown, the bioreactor system 1700 includes four pipe-based bioreactors 1702 connected in parallel to a fluid source 1708 containing a cell culture media 1710. During harvesting, an elevated harvest flow is induced in a given pipe-based bioreactor 1702 in order to introduce a shearing force sufficient to separate the cultured cells from the substrates disposed within the given pipe-based bioreactor 1702. As shown, the harvest flow can be comprised of cell culture media 1710 from fluid source 1708 or, alternatively, of a saline solution from another fluid source.

In some embodiments, each pipe-based bioreactor 1702 is harvested separately (i.e., one at a time) to enable increased flow rate and control. In some embodiments, for example, the harvest flow rate comprises a fluid velocity of 1000 to 3000 mm/s. Also, as shown in FIG. 17, each pipe-based bioreactor 1702 includes offset outlets 1724 and offset inlets 1722 to prevent regions of low flow during harvesting in place. Indeed, the incline and the offset outlets of pipe-based bioreactors, according to the various embodiments described herein, provide various advantages in the foregoing procedures for preparing cell-based meat products.

As shown in FIG. 17, a harvest flow operating in a counterclockwise direction (e.g., using a pump 1706) may separate cultured cells from the substrates within a given bioreactor 1702 and propels the cultured cells into a harvester mechanism 1712 (e.g., a catch and belt system) for collection. In some embodiments, the harvester mechanism 1712 gathers the cultured cells in one or more catch bins without opening or otherwise contaminating the system 1700. Embodiments of the harvester mechanism 1712 are described in greater detail below in relation to FIG. 18. As shown in FIG. 17, the cell culture media 1710 (or alternative harvesting fluid), along with the separated cultured cells, is circulated through the harvester mechanism 1712, returning to the system 1700 for a continuous flow. While the harvester mechanism 1712 is shown at a particular location within the bioreactor system 1700, in some embodiments the harvester mechanism 1712 is attached at another location (e.g., on the opposite side of the pipe-based bioreactors 1702) to allow for harvesting in the opposite (i.e., clockwise) direction.

As mentioned above, FIG. 18 illustrates an example embodiment of a harvester mechanism. More specifically, FIG. 18 illustrates a catch and belt system 1800, according to some embodiments, for gathering cultured cells separated from pipe-based bioreactors during harvesting in place. The catch and belt system 1800 is connected to a bioreactor system 1802 with a plurality of valves, such that a closed environment of the bioreactor system 1802 can be maintained throughout the various processes for preparing cell-based meat products disclosed herein. For instance, during harvesting in place, a bioreactor system valve 1820 is closed and catch system valves 1812 and 1818 are opened to direct the harvest flow into the catch and belt system 1800. Also, the catch and belt system 1800 comprises multiple catch bins 1804a-c for gathering (i.e., collecting) cultured cells from a harvest flow, such as described above in relation to FIG. 17. While the catch and belt system 1800 includes three catch bins 1804a-c, embodiments can include any number of catch bins 1804 for gathering cultured cells during harvesting in place.

As illustrated in FIG. 18, with the bioreactor system valve 1820 closed, the catch system entry valve 1812 open, and a catch system exit valve 1818 open, the harvest flow carrying cultured cells from a bioreactor system 1802 enters the catch and belt system 1800. Flowing in a counterclockwise direction, the harvest flow enters a first catch bin 1804a and, with bin entry and exit valves 1814a, 1816a open and other bin entry valves 1814b-c closed, cells begin to gather in the first catch bin 1804a. As the harvest flow passes through the first catch bin 1804a, cultures cells are gathered in the first catch bin 1804a as harvest flow fluid (e.g., cell culture media or saline solution) continues through the bin exit valve 1816a and back into the bioreactor system 1802.

As the first catch bin 1804a reaches full capacity, a pressure differential is detected by pressure sensors 1808, 1810. For instance, pressure detected by outlet pressure sensor 1818 is lower than pressure detected by inlet pressure sensor 1808 due to the first catch bin 1804a being obstructed by a full capacity of gathered cells. In response to detection of the pressure differential, harvest flow to the first catch bin 1804a is closed (i.e., cut off) via bin entry and exit valves 1814a, 1816a, and harvest flow to a second catch bin 1804b is opened via bin entry and exit valves 1814b, 1816b. The foregoing process is repeated to fill the second catch bin 1804b until a pressure differential is again detected by pressure sensors 1808, 1810, indicating that the second catch bin 1804 has reached full capacity. In response, harvest flow to the second catch bin 1804b is closed and harvest flow to the third catch bin 1804c is opened until a pressure differential is detected again. As mentioned previously, in some embodiments, additional catch bins 1804 can be incorporated to enable larger capacities of harvest cells. Conversely, fewer catch bin 1804 can be employed for smaller capacities of harvest cells.

Additionally, in response to any given catch bin 1804 being filled to full capacity, a harvest buffer 1806 is flowed through the full catch bin 1804 to remove the gathered cells to a belt filter 1828 (such as described below in relation to FIG. 19) or similar system for processing cells in preparation of comestible meat products. For instance, when the first catch bin 1804a reaches full capacity and harvest flow is diverted to another catch bin, buffer entry valve 1822a and buffer exit valve 1824a are opened to allow the harvest buffer 1806 to flow through the first catch bin 1804a.

Accordingly, the harvest buffer 1806 pushes and/or carries the collected cells from the first catch bin 1804a to the belt filter 1828 for further processing. In some embodiments, the harvest buffer 1806 flows through each catch bin 1804a-c individually and accumulates gathered cells into a feed hopper 1826 prior to further cell processing in the belt filter 1828. As illustrated, in some embodiments, the harvest buffer 1806 is configured to flow through each catch bin 1804 without entering the bioreactor system 1802.

As mentioned above, some embodiments utilize a belt filter to further process gathered cells in preparation of comestible meat products. For example, FIG. 19 illustrates a belt filter system 1900 according to one or more embodiments. As shown, harvested meat cells 1914 are fed into the belt filter system 1900 by a feed hopper 1902 (such as the feed hopper 1826 described above in relation to FIG. 18). More specifically, the feed hopper 1902 gradually drops harvested meat cells 1914 onto a porous conveyor belt 1904, where excess fluid drops through gravity section 1906 and exits via drain 1908. Additional fluid is extracted from the harvested meat cells 1914 utilizing a pressure section 1910. Finally, processed meat cells 1916 are collected in a receiving container 1912. In some embodiments, the belt filter system 1900 maintains a closed environment, such that sterility of the overall system can be maintained and the necessity for cleaning between meat cell preparation procedures reduced.

FIG. 20 illustrates a bioreactor system 2000 implementing a clean in place (CIP) procedure, according to one or more embodiments, for cleaning pipe-based bioreactors 2002 of the system 2000. As shown, the bioreactor system 2000 includes four pipe-based bioreactors 2002 connected in parallel to a fluid source 2008 containing a cell culture medium 2010. When cleaning one or more of the pipe-based bioreactors 2002, in some embodiments, cleaning fluid (e.g., caustic acid) from a cleaning module 2012 is flowed in a counterclockwise direction (e.g., using a pump 2006), through the pipe-based reactors 2002, returning to the cleaning module 2012 as illustrated. In some embodiments, for example, the cleaning fluid is flowed through each pipe-based bioreactor 2002 at a cleaning flow rate with a fluid velocity of 1 to 3 mm/s.

Moreover, as shown in FIG. 20, one or more of the pipe-based reactors 2002 can be cleaned in place without cleaning or otherwise disturbing the fluid source 2008 by shutting source valves 2016 and opening bioreactor system valves 2018 and cleaning valves 2020. Also, the fluid source 2008 can be cleaned in place separately, without cleaning or otherwise disturbing the pipe-based bioreactors 2002, by closing bioreactor system valves 2018 and opening source valves 2016 and cleaning valves 2020. Also, each pipe-based bioreactor 2002 can be cleaned in place separately (i.e., one at a time) by use of corresponding inlet valves 2004.

FIGS. 1-20, the corresponding text, and the examples provide a number of different methods, systems, and apparatuses for producing a comestible meat product. In addition to the foregoing, one or more embodiments can also be described in terms of flowcharts comprising acts for accomplishing a particular result, as shown in FIGS. 21 and 22. The acts described herein may be performed with more or fewer acts. Further, the acts may be performed in differing orders. Additionally, the acts described herein may be repeated or performed in parallel with one another or parallel with different instances of the same or similar acts.

As mentioned, FIGS. 21 and 22 illustrate flowcharts of two series of acts 2100 and 2200, respectively, and for producing a comestible meat product in accordance with one or more embodiments. While FIGS. 21 and 22 illustrate acts according to particular embodiments, alternative embodiments may omit, add to, reorder, and/or modify any of the acts shown in FIGS. 21 and 22.

FIG. 21 illustrates a flowchart of a series of acts 2100. By way of overview, the series of acts 2100 includes an act 2102 of flowing cells into an elongated bioreactor, and act 2104 of arresting flow to allow cells to settle and adhere to substrates of the elongated bioreactor, and an act 2106 of circulating cell culture media through the elongated bioreactor at an increasing flow rate to reduce shearing of cells while promoting growth.

The series of acts 2100 illustrated in FIG. 21 includes the act 2102 of flowing cells into an elongated bioreactor. For example, in some embodiments, the act 2102 comprises flowing cells into an elongated bioreactor for a first period of time. Also, in some embodiments, flowing cells into the elongated bioreactor comprises filling the elongated bioreactor with cell culture media and displacing the cell culture media within the elongated bioreactor with cells. In one or more embodiments, displacing the cell culture media within the elongated bioreactor comprises flowing cells into the elongated bioreactor at a flow rate configured to displace the cell culture media while at least partially reducing mixing of the cells with fluid within the elongated bioreactor.

Further, the series of acts 2100 illustrated in FIG. 21 includes the act 2104 of arresting flow to allow cells to settle and adhere to substrates of the elongated bioreactor. In particular, the act 2104 comprises at least partially arresting flow of material through the elongated bioreactor for a second period of time to allow at least a portion of the cells to settle and adhere to one or more substrates within the elongated bioreactor. Additionally, in some embodiments, the act 2104 comprises, in response to allowing the at least a portion of the cells to settle and adhere to the one or more substrates, rotating the one or more substrates about a longitudinal axis relative to the elongated bioreactor, and allowing an additional portion of the cells to settle and adhere to one or more opposing surfaces of the one or more substrates within the elongated bioreactor by at least partially arresting flow of material through the elongated bioreactor for an additional period of time.

In one or more embodiments. the act 2104 further comprises continuously rotating the one or more substrates about a longitudinal axis while at least partially arresting flow of material through the elongated bioreactor for the second period of time to allow the at least a portion of the cells to settle and adhere to the one or more substrates within the elongated bioreactor.

Further, the series of acts 2100 illustrated in FIG. 21 includes the act 2106 of circulating cell culture media through the elongated bioreactor at an increasing flow rate to reduce shearing of cells while promoting growth. In particular, the act 2106 comprises circulating cell culture media through the elongated bioreactor for a third period of time at a progressively increasing flow rate to prevent shearing of the adhered cells from the one or more substrates while promoting growth of the adhered cells.

Moreover, in some embodiments, the series of acts 2100 also includes an act (not shown in FIG. 21) for harvesting meat cells from the elongated bioreactor by flowing fluid through the elongated bioreactor at an elevated flow rate compared to a maximum flow rate of the progressively increasing flow rate, the elevated flow rate configured to separate the adhered cells from the one or more substrates. While also not shown in FIG. 21, in one or more embodiments, the series of acts 2100 further comprises cleaning the elongated bioreactor by flowing fluid through the elongated bioreactor at a further elevated flow rate configured to separate materials remaining on the one or more substrates after harvesting.

FIG. 22 illustrates a flowchart of a series of acts 2200. By way of overview, the series of acts 2200 includes an act 2202 of growing cells within a plurality of interconnected elongated bioreactors, an act 2204 of closing valves to bioreactors other than at least one bioreactor of the plurality of interconnected elongated bioreactors, an act 2206 of harvesting cells from the at least one bioreactor, and an act 2208 of cleaning the at least one bioreactor in place by flowing fluid therethrough.

The series of acts 2200 illustrated in FIG. 22 includes the act 2202 of growing cells within a plurality of interconnected elongated bioreactors. For example, in some embodiments, the act 2202 comprises growing a plurality of meat cells within a plurality of interconnected elongated bioreactors by circulating cell culture media through the plurality of interconnected elongated bioreactors at one or more cultivation flow rates. In some embodiments, the act 2202 comprises growing a plurality of meat cells within a plurality of interconnected elongated bioreactors by circulating cell culture media through the plurality of interconnected elongated bioreactors at one or more cultivation flow rates.

Further, the series of acts 2200 illustrated in FIG. 22 includes the act 2204 of closing valves to bioreactors other than at least one bioreactor of the plurality of interconnected elongated bioreactors. In some embodiments, for example, the act 2204 comprises selectively flowing fluid through at least one elongated bioreactor by opening one or more valves connected to the at least one elongated bioreactor and closing one or more valves connected to one or more other elongated bioreactors of the plurality of interconnected elongated bioreactors. Also, in some embodiments, closing the one or more valves connected to the one or more other elongated bioreactors increases a flow rate within the at least one elongated bioreactor. Moreover, in some embodiments, selectively flowing fluid through the at least one elongated bioreactor comprises seeding or cultivating meat cells within the at least one elongated bioreactor while maintaining a closed environment of the one or more other elongated bioreactors.

Further, the series of acts 2200 illustrated in FIG. 22 includes the act 2206 for harvesting cells from the at least one bioreactor. For example, in some embodiments, the act 2206 includes harvesting meat cells from within the plurality of interconnected elongated bioreactors by flowing fluid through the plurality of interconnected elongated bioreactors at an elevated flow rate compared to the one or more cultivation flow rates.

In one or more embodiments, the acts 2204 and 2206 comprise selectively harvesting meat cells from at least one elongated bioreactor of the plurality of interconnected elongated bioreactors by closing valves to one or more other bioreactors of the plurality of interconnected elongated bioreactors and flowing fluid through the at least one bioreactor at an elevated flow rate compared to the one or more cultivation flow rates. Also, in some embodiments, selectively harvesting meat cells from the at least one elongated bioreactor further comprises collecting harvested meat cells within a closed environment utilizing a harvester mechanism.

Further, the series of acts 2200 illustrated in FIG. 22 includes the act 2208 of cleaning the at least one bioreactor in place by flowing fluid therethrough. In some embodiments, for example, the act 2208 comprises selectively flowing fluid through the at least one elongated bioreactor comprises cleaning the at least one elongated bioreactor in place while maintaining a closed environment of the one or more other elongated bioreactors. In one or more embodiments, the act 2208 comprises, in response to selectively harvesting meat cells from the at least one elongated bioreactor, selectively cleaning in place the at least one elongated bioreactor by flowing a cleaning fluid through the at least one elongated bioreactor without flowing the cleaning fluid through the one or more other elongated bioreactors. Further, some embodiments include selectively steaming the at least one elongated bioreactor by closing valves to the one or more other elongated bioreactors of the plurality of interconnected elongated bioreactors and flowing steam through the at least one elongated bioreactor.

In one or more embodiments, the act 2208 comprises cleaning the elongated bioreactor in place by flowing fluid through the elongated bioreactor after harvesting meat cells from within an elongated bioreactor. Also, in some embodiments, the act 2208 further comprises sanitizing the elongated bioreactor in place by flowing steam through the elongated bioreactor. In addition, in some embodiments, flowing steam through the elongated bioreactor is done in a direction opposite to a direction which fluid flows through the elongated bioreactor during seeding of the elongated bioreactor. Additionally, when flowing steam through the elongated bioreactor, in one or more embodiments, the elongated bioreactor is mounted at an incline relative to a ground surface to reduce accumulation of condensation within the elongated bioreactor. In one or more embodiments, cleaning the elongated bioreactor in place by flowing the fluid through the elongated bioreactor comprises flowing the fluid through the elongated bioreactor at a flow rate configured to separate materials adhering to one or more surfaces within the elongated bioreactor. Also, in some embodiments, cleaning the elongated bioreactor in place by flowing the fluid through the elongated bioreactor comprises flowing a cleaning solution through the elongated bioreactor.

Moreover, in some embodiments, the series of acts 2200 also includes an act (not shown in FIG. 22) for, prior to growing the plurality of meat cells within the plurality of interconnected elongated bioreactors, selectively cleaning in place the at least one elongated bioreactor by closing valves connected to the one or more other elongated bioreactors of the plurality of interconnected elongated bioreactors and flowing cleaning solution through the at least one elongated bioreactor. Further, in one or more embodiments, the plurality of interconnected elongated bioreactors is mounted at an incline relative to a ground surface to reduce accumulation of gas bubbles within each elongated bioreactor of the plurality of interconnected elongated bioreactors during cultivation. Further still, in one or more embodiments, each elongated bioreactor of the plurality of interconnected elongated bioreactors further comprises offset inlets and offset outlets configured to reduce accumulation of fluids therein.

In accordance with common practice, the various features illustrated in the drawings may not be drawn to scale. The illustrations presented in the present disclosure are not meant to be actual views of any particular apparatus (e.g., device, system, etc.) or method, but are merely idealized representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or all operations of a particular method.

Terms used herein and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc. For example, the use of the term "and/or" is intended to be construed in this manner.

Further, any disjunctive word or phrase presenting two or more alternative terms, whether in the description, claims, or drawings, should be understood to contemplate the possibilities of including one of the terms, either of the terms, or both terms. For example, the phrase "A or B" should be understood to include the possibilities of "A" or "B" or "A and B."

However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

Additionally, the use of the terms "first," "second," "third," etc., are not necessarily used herein to connote a specific order or number of elements. Generally, the terms "first," "second," "third," etc., are used to distinguish between different elements as generic identifiers. Absent a showing that the terms "first," "second," "third," etc., connote a specific order, these terms should not be understood to connote a specific order. Furthermore, absent a showing that the terms "first," "second," "third," etc., connote a specific number of elements, these terms should not be understood to connote a specific number of elements. For example, a first widget may be described as having a first side and a second widget may be described as having a second side. The use of the term "second side" with respect to the second widget may be to distinguish such side of the second widget from the "first side" of the first widget and not to connote that the second widget has two sides.

All examples and conditional language recited herein are intended for pedagogical objects to aid the reader in understanding the invention and the concepts contributed by the inventor to furthering the art and are to be construed as being without limitation to such specifically recited examples and conditions. Although embodiments of the present disclosure have been described in detail, it should be understood that the various changes, substitutions, and alterations could be made hereto without departing from the spirit and scope of the present disclosure.

The present invention may be embodied in other specific forms without departing from its spirit or essential characteristics. Indeed, the described embodiments are to be considered in all respects only as illustrative and not restrictive. For example, the methods described herein may be performed with less or more steps/acts or the steps/acts may be performed in differing orders. Additionally, the steps/acts described herein may be repeated or performed in parallel to one another or in parallel to different instances of the same or similar steps/acts. The scope of the invention is, therefore, indicated by the appended claims rather than by the foregoing description. All changes that come within the meaning and range of equivalency of the claims are to be embraced within their scope.

What is claimed is:

1. A method for producing a comestible meat product, the method comprising:

growing a plurality of meat cells on respective pluralities of substrates disposed within a plurality of interconnected elongated bioreactors by circulating cell culture media through each elongated bioreactor of the plurality of interconnected elongated bioreactors at one or more cultivation flow rates with a substantially uniform distribution of internal pressure within each elongated bioreactor, wherein an elongated enclosure of each elongated bioreactor of the plurality of interconnected elongated bioreactors forms a closeable environment and defines a substantially straight axial flow path extending from a respective inlet to a respective outlet of the elongated enclosure along its longitudinal axis; and harvesting meat cells from within the plurality of interconnected elongated bioreactors by flowing fluid from the respective inlet to the respective outlet of each elongated bioreactor of the plurality of interconnected elongated bioreactors at an elevated flow rate compared to the one or more cultivation flow rates.

2. The method of claim 1, further comprising circulating the cell culture media with a substantially uniform distribution of a temperature or a PH level within each elongated bioreactor of the plurality of interconnected elongated bioreactors.

3. The method of claim 1, further comprising circulating the cell culture media within a closed environment comprising the plurality of interconnected elongated bioreactors connected in parallel to a fluid source containing an at least partially liquid growth medium.

4. The method of claim 3, further comprising, in response to harvesting meat cells from within the plurality of interconnected elongated bioreactors, cleaning in place the fluid source by closing one or more valves connected to the plurality of interconnected elongated bioreactors, opening one or more valves connected to the fluid source, and flowing a cleaning fluid through the fluid source without flowing the cleaning fluid through the plurality of interconnected elongated bioreactors.

5. The method of claim 1, further comprising selectively steaming at least one elongated bioreactor in place by:

opening one or more valves connected to the at least one elongated bioreactor;

closing one or more valves connected to one or more other elongated bioreactors of the plurality of interconnected elongated bioreactors; and flowing steam through the at least one elongated bioreactor within a closed environment formed between a steam source, the at least one elongated bioreactor, and a steam trap.

6. The method of claim 1, further comprising selectively flowing fluid through at least one elongated bioreactor by opening one or more valves connected to the at least one elongated bioreactor and closing one or more valves connected to one or more other elongated bioreactors of the plurality of interconnected elongated bioreactors.

7. The method of claim 6, further comprising selectively flowing fluid through the at least one elongated bioreactor without flowing fluid through the one or more other elongated bioreactors.

8. The method of claim 6, wherein selectively flowing fluid through the at least one elongated bioreactor comprises seeding or cultivating meat cells within the at least one elongated bioreactor while maintaining a closed environment of the one or more other elongated bioreactors.

9. The method of claim 8, further comprising selectively flowing fluid through at least one additional elongated bioreactor of the plurality of interconnected elongated bioreactors to seed or cultivate meat cells within the at least one additional elongated bioreactor by closing the one or more valves connected to the at least one elongated bioreactor and opening one or more valves connected to the at least one additional elongated bioreactor.

10. The method of claim 6, wherein selectively flowing fluid through the at least one elongated bioreactor comprises cleaning the at least one elongated bioreactor in place while maintaining a closed environment within each of the one or more other elongated bioreactors.

11. A method for producing a comestible meat product, the method comprising:

growing a plurality of meat cells within a plurality of interconnected elongated bioreactors by circulating cell culture media in unobstructed flow from an inlet of at least one elongated bioreactor of the plurality of interconnected elongated bioreactors to one or more substrates of the at least one elongated bioreactor at one or more cultivation flow rates between 0.5 mm/s and 5 mm/s with a substantially uniform distribution of internal pressure within the at least one elongated bioreactor;

selectively harvesting meat cells from the at least one elongated bioreactor of the plurality of interconnected elongated bioreactors by closing valves connected to one or more other elongated bioreactors of the plurality of interconnected elongated bioreactors and flowing fluid from the inlet to an outlet of the at least one elongated bioreactor at a harvesting flow rate that is at least 200 times the one or more cultivation flow rates; and cleaning the at least one elongated bioreactor in place by circulating fluid from the inlet to the outlet of the at least one elongated bioreactor at a cleaning flow rate that is higher than the harvesting flow rate.

12. The method of claim 11, wherein selectively harvesting meat cells from the at least one elongated bioreactor further comprises collecting harvested meat cells within a closed environment utilizing a harvester mechanism.

13. The method of claim 11, further comprising, prior to growing the plurality of meat cells within the plurality of interconnected elongated bioreactors, selectively cleaning in place the at least one elongated bioreactor by closing valves connected to the one or more other elongated bioreactors of the plurality of interconnected elongated bioreactors and flowing cleaning solution through the at least one elongated bioreactor.

14. The method of claim 13, further comprising:
in response to selectively cleaning in place the at least one elongated bioreactor, selectively growing an additional plurality of meat cells within the at least one elongated bioreactor; and
selectively harvesting the additional plurality of meat cells from the at least one elongated bioreactor.

15. The method of claim 11, further comprising, in response to selectively harvesting meat cells from the at least one elongated bioreactor, selectively cleaning in place the at least one elongated bioreactor by flowing a cleaning fluid through the at least one elongated bioreactor without flowing the cleaning fluid through the one or more other elongated bioreactors.

16. The method of claim 11, further comprising selectively steaming the at least one elongated bioreactor by closing valves connected to the one or more other elongated bioreactors of the plurality of interconnected elongated bioreactors and flowing steam through the at least one elongated bioreactor.

17. The method of claim 16, wherein selectively steaming the at least one elongated bioreactor comprises flowing steam from the outlet of the at least one elongated bioreactor to the inlet of the at least one elongated bioreactor.

18. The method of claim 11, wherein the plurality of interconnected elongated bioreactors is mounted at an incline relative to a ground surface to reduce accumulation of gas bubbles within each elongated bioreactor of the plurality of interconnected elongated bioreactors during cultivation.

19. The method of claim 11, wherein each elongated bioreactor of the plurality of interconnected elongated bioreactors further comprises offset inlets and offset outlets, wherein the offset inlets and offset outlets are:
disposed at opposing ends of each elongated bioreactor,
offset relative to a longitudinal axis of each elongated bioreactor, and
configured to reduce accumulation of fluids therein.

20. The method of claim 11, wherein circulating the cell culture media through the plurality of interconnected elongated bioreactors at the one or more cultivation flow rates comprises progressively increasing flow to substantially prevent removal of meat cells from the plurality of interconnected elongated bioreactors while circulating the cell culture media.

* * * * *